(12) United States Patent
Conklin et al.

(10) Patent No.: US 11,690,714 B2
(45) Date of Patent: Jul. 4, 2023

(54) HYBRID HEART VALVES ADAPTED FOR POST-IMPLANT EXPANSION

(71) Applicant: Edwards Lifesciences Corporation, Irvine, CA (US)

(72) Inventors: Brian S. Conklin, Orange, CA (US); Qinggang Zeng, Mission Viejo, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 354 days.

(21) Appl. No.: 16/914,255

(22) Filed: Jun. 26, 2020

(65) Prior Publication Data
US 2020/0323633 A1 Oct. 15, 2020

Related U.S. Application Data

(62) Division of application No. 15/199,743, filed on Jun. 30, 2016, now Pat. No. 10,695,170.
(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2433* (2013.01);
(Continued)

(58) Field of Classification Search
CPC .... A61F 2/2418; A61F 2/2412; A61F 2/2409; A61F 2/07; A61F 2250/0048; A61F 2250/0063; A61F 2/24
See application file for complete search history.

(56) References Cited

U.S. PATENT DOCUMENTS 3,143,742 A   8/1964 Cromie
3,320,972 A   5/1967 High et al.
(Continued)

FOREIGN PATENT DOCUMENTS

CN   102883684 A   1/2013
EP   0125393 A1   11/1984
(Continued)

OTHER PUBLICATIONS

Krakow, "3F Therapeutics, Inc. Announces the First Clinical Implantation of the 3F Enable Aortic Heart Valve.TM., a Patented, Sutureless Implantation, Replacement Heart Valve intended to Save Valuable Surgery Time and Reduce Time RelatedComplications . . . "Healthcare Sales & Marketing Network News Feed, Jan. 18, 2005, pp. 1-2.
(Continued)

*Primary Examiner* — Seema Mathew
(74) *Attorney, Agent, or Firm* — Guy Cumberbatch

(57) ABSTRACT

A hybrid prosthetic heart valve configured to replace a native heart valve and having a support frame configured to be expanded post implant in order to receive and/or support an expandable prosthetic heart valve therein (a valve-in-valve procedure). The prosthetic heart valve may be configured to have a generally rigid and/or expansion-resistant configuration when initially implanted to replace a native valve (or other prosthetic heart valve), but to assume a generally expanded form when subjected to an outward force such as that provided by a dilation balloon or other mechanical expander. An inflow stent frame is expandable for anchoring the valve in place, and may have an outflow end that is collapsible for delivery and expandable post-implant to facilitate a valve-in-valve procedure.

19 Claims, 13 Drawing Sheets

Related U.S. Application Data

(60) Provisional application No. 62/188,467, filed on Jul. 2, 2015.

(52) U.S. Cl.
CPC .......... A61F 2210/0004 (2013.01); A61F 2210/0057 (2013.01); A61F 2220/0075 (2013.01); A61F 2230/0052 (2013.01); A61F 2230/0054 (2013.01); A61F 2230/0067 (2013.01); A61F 2250/001 (2013.01); A61F 2250/0012 (2013.01); A61F 2250/0018 (2013.01); A61F 2250/0021 (2013.01); A61F 2250/0039 (2013.01); A61F 2250/0048 (2013.01); A61F 2250/0089 (2013.01)

(56) References Cited

U.S. PATENT DOCUMENTS

| | | |
|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,656,185 A | 4/1972 | Carpentier |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 4,035,849 A | 7/1977 | Angell et al. |
| 4,055,861 A | 11/1977 | Carpentier et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,164,046 A | 8/1979 | Cooley |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,602,911 A | 7/1986 | Ahmadi et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovii et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,147,391 A | 9/1992 | Lane |
| 5,163,955 A | 11/1992 | Love et al. |
| 5,201,880 A | 4/1993 | Wright et al. |
| 5,258,021 A | 11/1993 | Duran |
| 5,258,023 A | 11/1993 | Reger |
| 5,306,296 A | 4/1994 | Wright et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,450,860 A | 9/1995 | O'Connor |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,496,336 A | 3/1996 | Cosgrove et al. |
| 5,500,016 A | 3/1996 | Fisher |
| 5,533,515 A | 7/1996 | Colter et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,593,435 A | 1/1997 | Carpentier et al. |
| 5,607,471 A | 3/1997 | Seguin et al. |
| 5,626,607 A | 5/1997 | Malecki et al. |
| 5,628,789 A | 5/1997 | Vanney et al. |
| 5,674,279 A | 10/1997 | Wright et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,776,189 A | 7/1998 | Khalid |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,066 A | 10/1998 | Gross |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,888,240 A | 3/1999 | Carpentier et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,972,030 A | 10/1999 | Garrison et al. |

(56) References Cited

U.S. PATENT DOCUMENTS

| | | |
|---|---|---|
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,264,611 B1 | 7/2001 | Ishikawa et al. |
| 6,322,526 B1 | 11/2001 | Rosenman et al. |
| 6,332,893 B1 | 12/2001 | Mortier et al. |
| 6,348,068 B1 | 2/2002 | Campbell et al. |
| 6,350,282 B1 | 2/2002 | Eberhardt |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,425,916 B1 | 7/2002 | Garrison et al. |
| 6,491,624 B1 | 12/2002 | Lotfi |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,764,510 B2 | 7/2004 | Vidlund et al. |
| 6,773,457 B2 | 8/2004 | Ivancev et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,018,404 B2 | 3/2006 | Holmberg et al. |
| 7,037,333 B2 | 5/2006 | Myers et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,261,732 B2 | 8/2007 | Justino |
| 7,276,084 B2 | 10/2007 | Yang et al. |
| 7,294,148 B2 | 11/2007 | McCarthy |
| 7,381,218 B2 | 6/2008 | Schreck |
| 7,393,360 B2 | 7/2008 | Spenser et al. |
| 7,399,315 B2 | 7/2008 | Iobbi |
| 7,452,376 B2 | 11/2008 | Lim et al. |
| 7,462,191 B2 | 12/2008 | Spenser et al. |
| 7,470,285 B2 | 12/2008 | Nugent et al. |
| 7,510,575 B2 | 3/2009 | Spenser et al. |
| 7,524,330 B2 | 4/2009 | Berreklouw |
| 7,534,261 B2 | 5/2009 | Friedman |
| 7,556,646 B2 | 7/2009 | Yang et al. |
| 7,585,321 B2 | 9/2009 | Cribier |
| 7,625,403 B2 | 12/2009 | Krivoruchko |
| 7,780,723 B2 | 8/2010 | Taylor |
| 7,806,927 B2 | 10/2010 | Styrc |
| 7,871,436 B2 | 1/2011 | Ryan et al. |
| 7,998,151 B2 | 8/2011 | St. Goar et al. |
| 8,226,707 B2 | 7/2012 | White |
| 8,246,677 B2 | 8/2012 | Ryan |
| 8,308,798 B2 | 11/2012 | Pintor et al. |
| 8,323,337 B2 | 12/2012 | Gurskis et al. |
| 8,348,998 B2 | 1/2013 | Pintor et al. |
| 8,496,700 B2 | 7/2013 | Edoga et al. |
| 8,500,802 B2 | 8/2013 | Lane et al. |
| 8,579,964 B2 | 11/2013 | Lane et al. |
| 9,504,563 B2 * | 11/2016 | Pintor .................. A61F 2/2418 |
| 10,080,653 B2 * | 9/2018 | Conklin ............... A61F 2/2409 |
| 11,065,112 B2 * | 7/2021 | Gassler ............... A61F 2/2409 |
| 11,083,574 B2 * | 8/2021 | Sievers ................ A61F 2/2409 |
| 2001/0021872 A1 | 9/2001 | Bailey et al. |
| 2001/0021874 A1 | 9/2001 | Carpentier et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0062150 A1 | 5/2002 | Campbell et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0173842 A1 * | 11/2002 | Buchanan ............. A61F 2/2409 |
| | | 623/2.14 |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0033009 A1 | 2/2003 | Gabbay |
| 2003/0036795 A1 | 2/2003 | Andersen et al. |
| 2003/0040792 A1 | 2/2003 | Gabbay |
| 2003/0040793 A1 | 2/2003 | Marquez |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0199971 A1 | 10/2003 | Tower et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Iobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0249452 A1 | 12/2004 | Adams et al. |
| 2004/0249453 A1 | 12/2004 | Cartledge et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |

(56) References Cited

U.S. PATENT DOCUMENTS

| | | |
|---|---|---|
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0096739 A1 | 5/2005 | Cao |
| 2005/0131533 A1 | 6/2005 | Alfieri et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240200 A1 | 10/2005 | Bergheim |
| 2005/0240259 A1 | 10/2005 | Sisken et al. |
| 2005/0251251 A1 | 11/2005 | Cribier |
| 2005/0251252 A1 | 11/2005 | Stobie |
| 2005/0256567 A1 | 11/2005 | Lim et al. |
| 2005/0256568 A1 | 11/2005 | Lim et al. |
| 2005/0261765 A1 | 11/2005 | Liddicoat |
| 2005/0267572 A1 | 12/2005 | Schoon et al. |
| 2005/0278022 A1 | 12/2005 | Lim |
| 2005/0283231 A1 | 12/2005 | Haug et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025857 A1 | 2/2006 | Bergheim et al. |
| 2006/0025858 A1 | 2/2006 | Alameddine |
| 2006/0030885 A1 | 2/2006 | Hyde |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0043435 A1 | 2/2007 | Seguin et al. |
| 2007/0067029 A1 | 3/2007 | Gabbay |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0100441 A1 | 5/2007 | Kron et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0021546 A1 | 1/2008 | Patz et al. |
| 2008/0027483 A1 | 1/2008 | Cartledge et al. |
| 2008/0033543 A1 | 2/2008 | Gurskis et al. |
| 2008/0065198 A1 | 3/2008 | Quintessenza |
| 2008/0114452 A1 | 5/2008 | Gabbay |
| 2008/0119875 A1 | 5/2008 | Ino et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0200980 A1 | 8/2008 | Robin et al. |
| 2008/0208327 A1 | 8/2008 | Rowe |
| 2008/0208329 A1 | 8/2008 | Bishop et al. |
| 2008/0215144 A1 | 9/2008 | Ryan et al. |
| 2008/0228263 A1 | 9/2008 | Ryan |
| 2008/0243246 A1 | 10/2008 | Ryan et al. |
| 2008/0269878 A1 | 10/2008 | Iobbi |
| 2008/0275549 A1 | 11/2008 | Rowe |
| 2008/0281411 A1 | 11/2008 | Berreklouw |
| 2008/0319543 A1 | 12/2008 | Lane |
| 2009/0005863 A1 | 1/2009 | Goetz et al. |
| 2009/0036903 A1 | 2/2009 | Ino et al. |
| 2009/0082857 A1 | 3/2009 | Lashinski et al. |
| 2009/0093876 A1 | 4/2009 | Niizan et al. |
| 2009/0192599 A1 | 7/2009 | Lane et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0216322 A1 | 8/2009 | Le et al. |
| 2009/0281609 A1 | 11/2009 | Benichou et al. |
| 2010/0076548 A1 | 3/2010 | Konno |
| 2010/0076549 A1 | 3/2010 | Keidar et al. |

(56) References Cited

U.S. PATENT DOCUMENTS

| | | |
|---|---|---|
| 2010/0161036 A1 | 6/2010 | Pintor et al. |
| 2010/0249894 A1 | 9/2010 | Oba et al. |
| 2010/0249908 A1 | 9/2010 | Chau et al. |
| 2010/0256752 A1 | 10/2010 | Forster et al. |
| 2010/0331972 A1 | 12/2010 | Pintor et al. |
| 2011/0022165 A1 | 1/2011 | Oba et al. |
| 2011/0147251 A1 | 6/2011 | Hodshon et al. |
| 2011/0166636 A1 | 7/2011 | Rowe |
| 2011/0178597 A9 | 7/2011 | Navia et al. |
| 2011/0264207 A1 | 10/2011 | Bonhoeffer et al. |
| 2012/0065729 A1 | 3/2012 | Pintor et al. |
| 2012/0078357 A1* | 3/2012 | Conklin ............... A61F 2/2415 623/2.18 |
| 2012/0150288 A1 | 6/2012 | Hodshon et al. |
| 2013/0053949 A1 | 2/2013 | Pintor et al. |
| 2013/0116777 A1 | 5/2013 | Pintor et al. |
| 2014/0188221 A1* | 7/2014 | Chung ............... A61F 2/2409 623/2.18 |
| 2015/0119982 A1 | 4/2015 | Quill et al. |
| 2015/0366664 A1* | 12/2015 | Guttenberg ........... A61F 2/2412 623/2.17 |
| 2017/0172739 A1* | 6/2017 | Chang ............... A61F 2/2439 |
| 2018/0289475 A1* | 10/2018 | Chung ............... A61F 2/2409 |

FOREIGN PATENT DOCUMENTS

| | | |
|---|---|---|
| EP | 0143246 A2 | 6/1985 |
| EP | 0338994 A1 | 10/1989 |
| EP | 1034753 A1 | 9/2000 |
| EP | 1755459 A2 | 2/2007 |
| EP | 1804726 A1 | 7/2007 |
| EP | 1958598 A1 | 8/2008 |
| SU | 1116573 A1 | 7/1985 |
| SU | 1697790 A1 | 12/1991 |
| WO | 9213502 A1 | 8/1992 |
| WO | 9742871 A1 | 11/1997 |
| WO | 2015196152 A1 | 12/2015 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

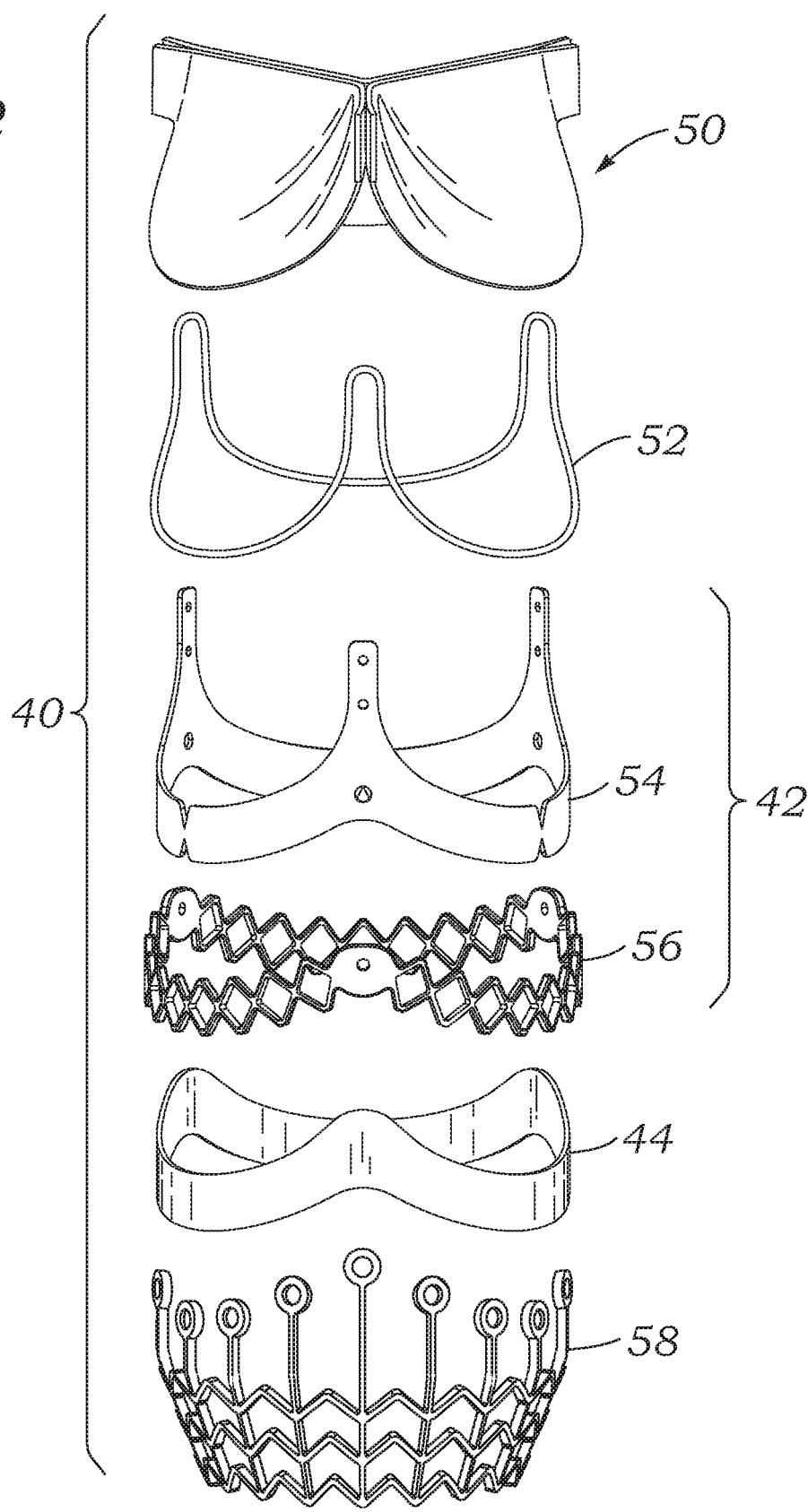

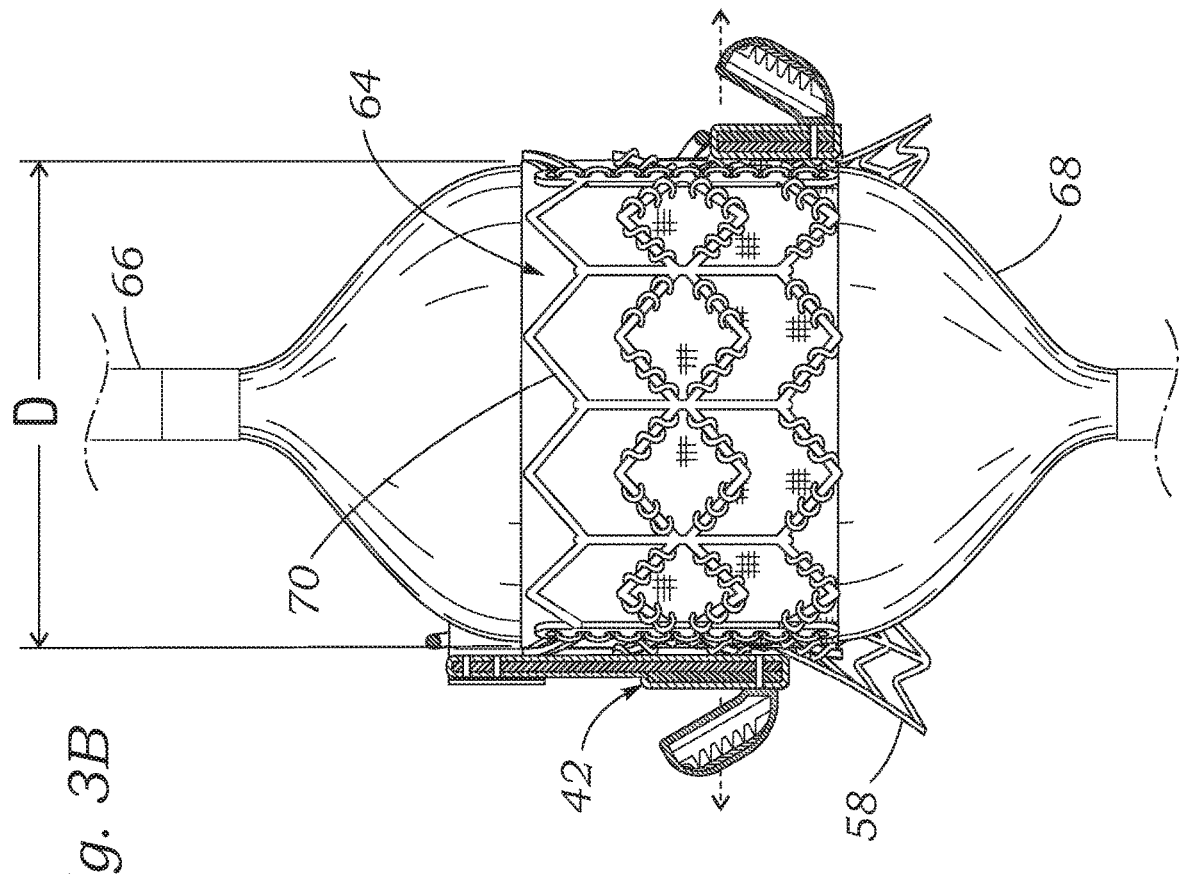
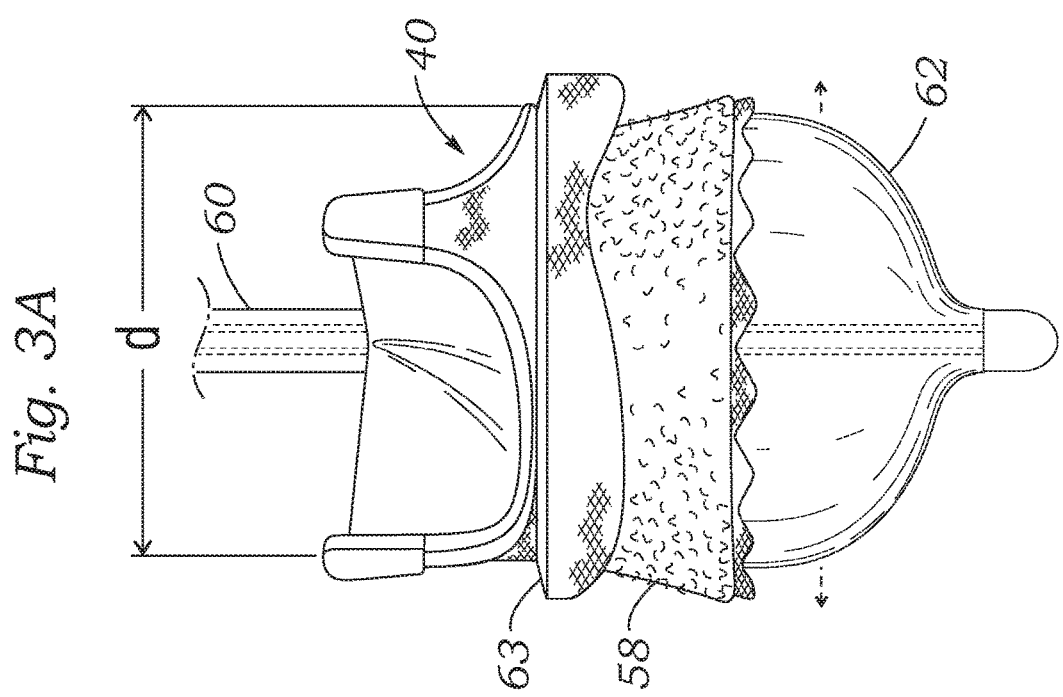

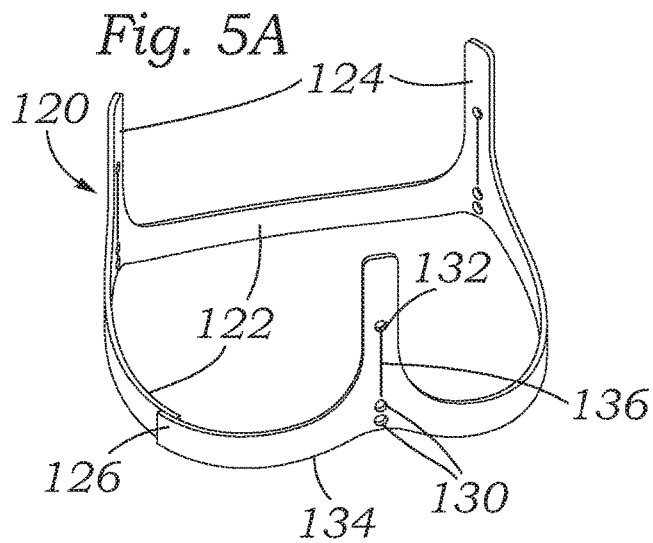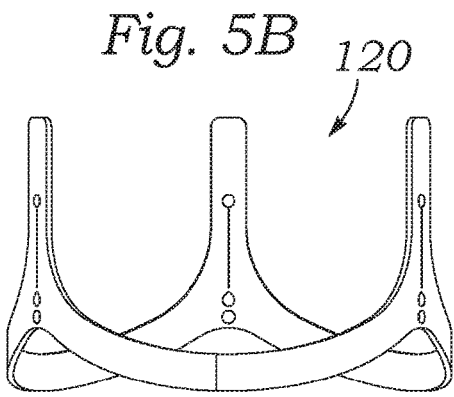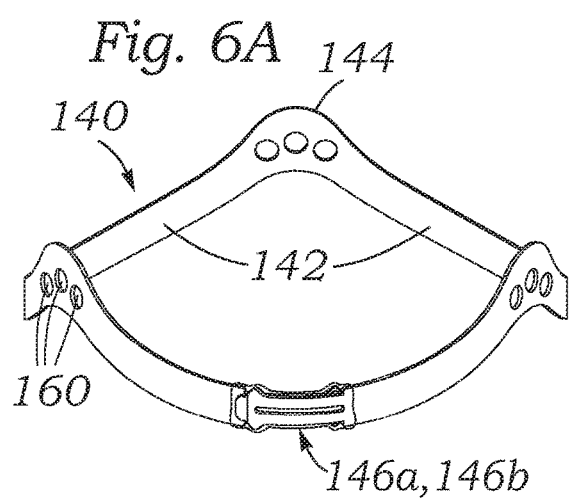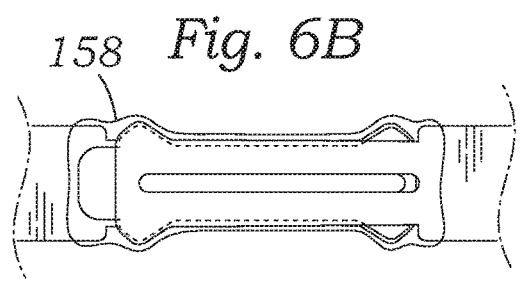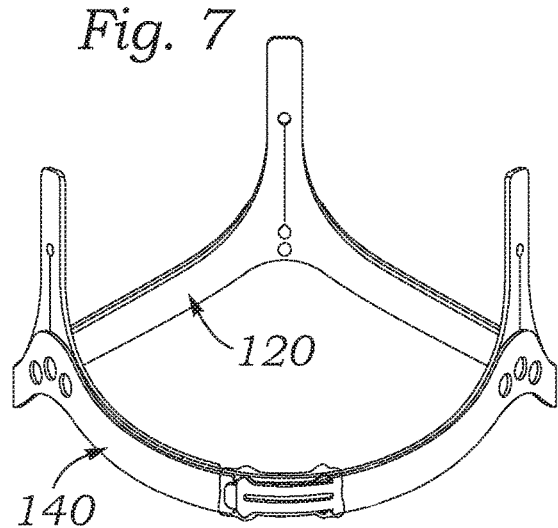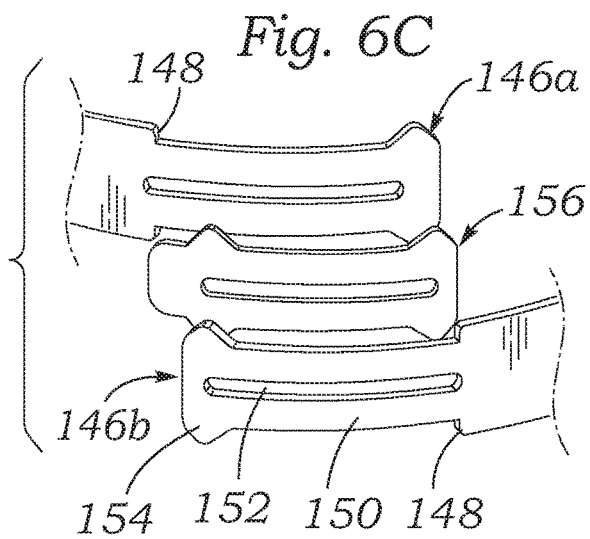

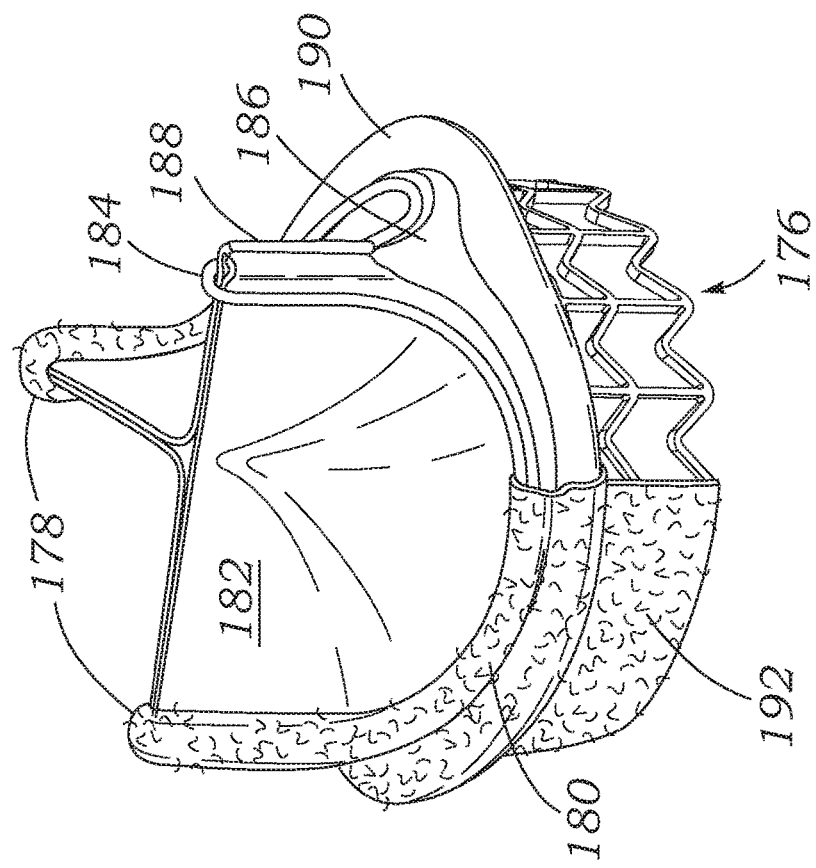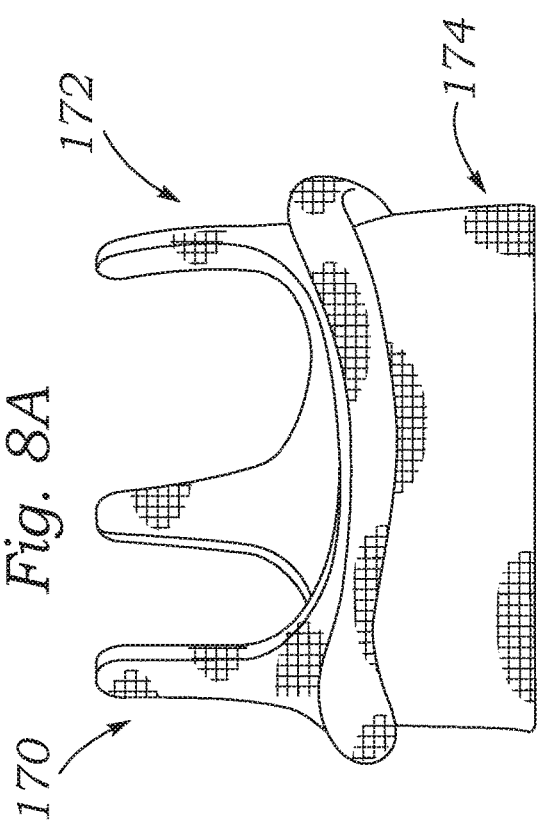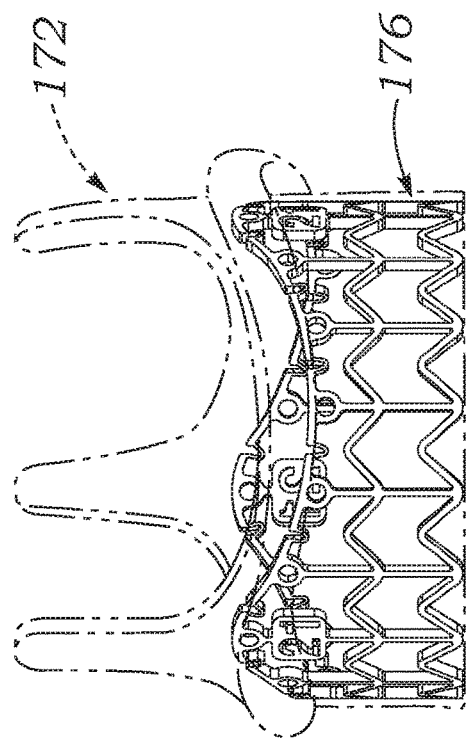

Fig. 10A
Fig. 10B
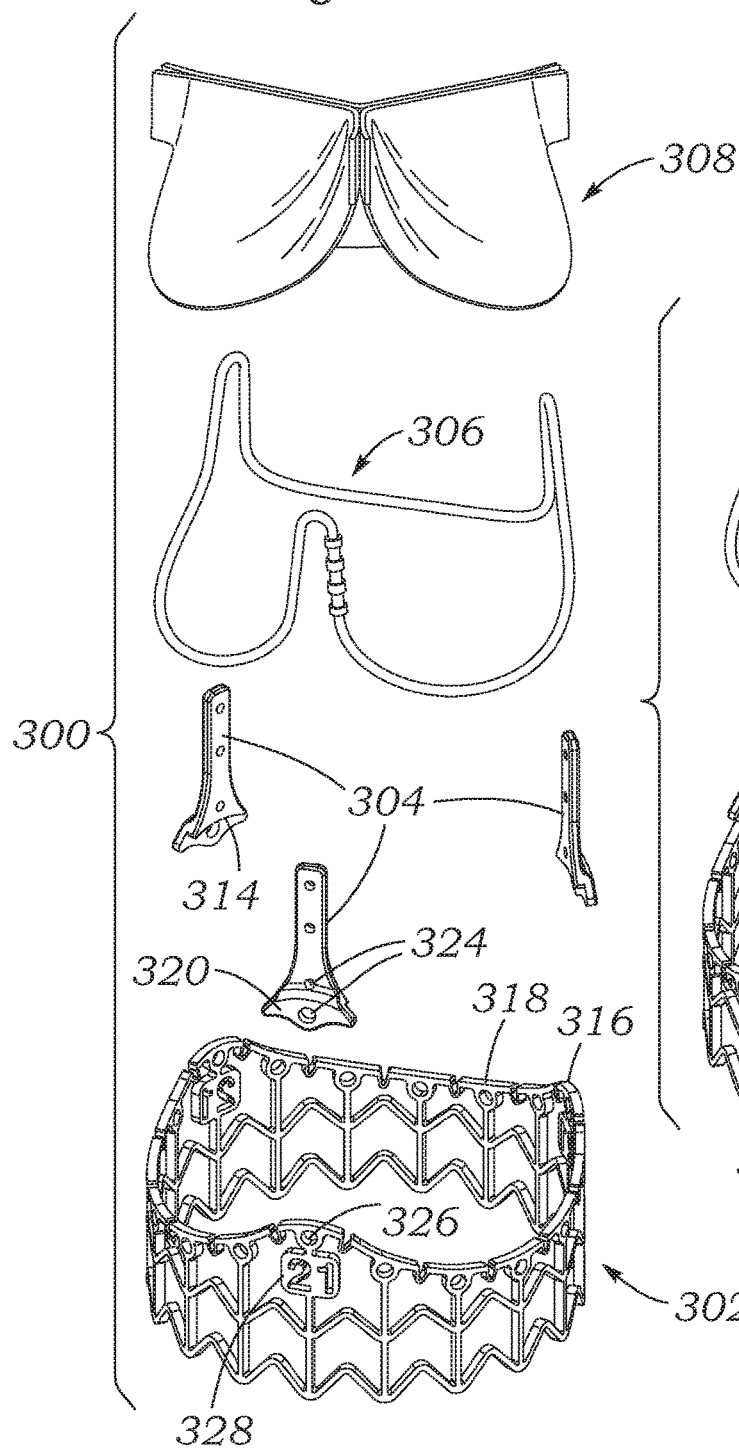
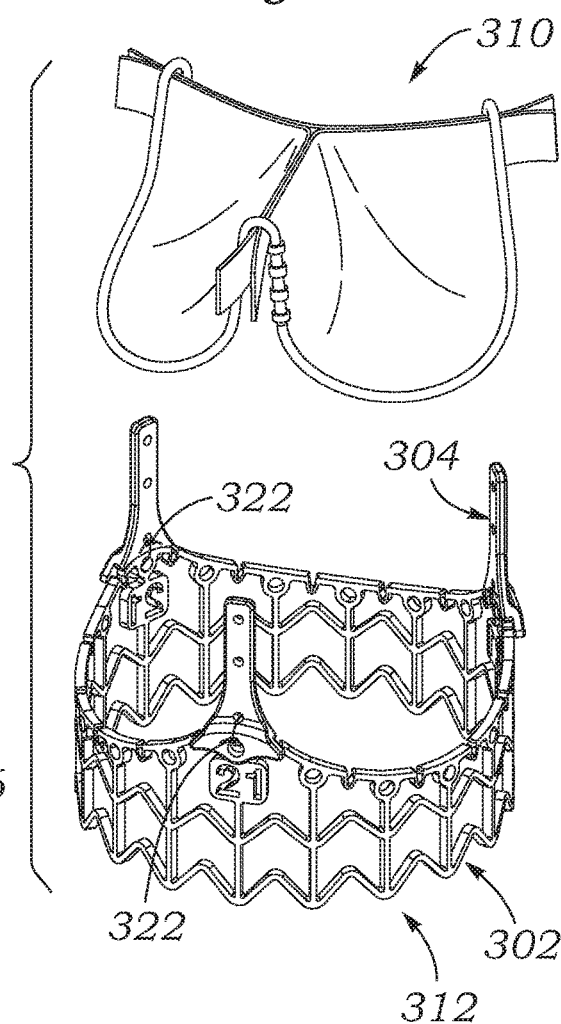

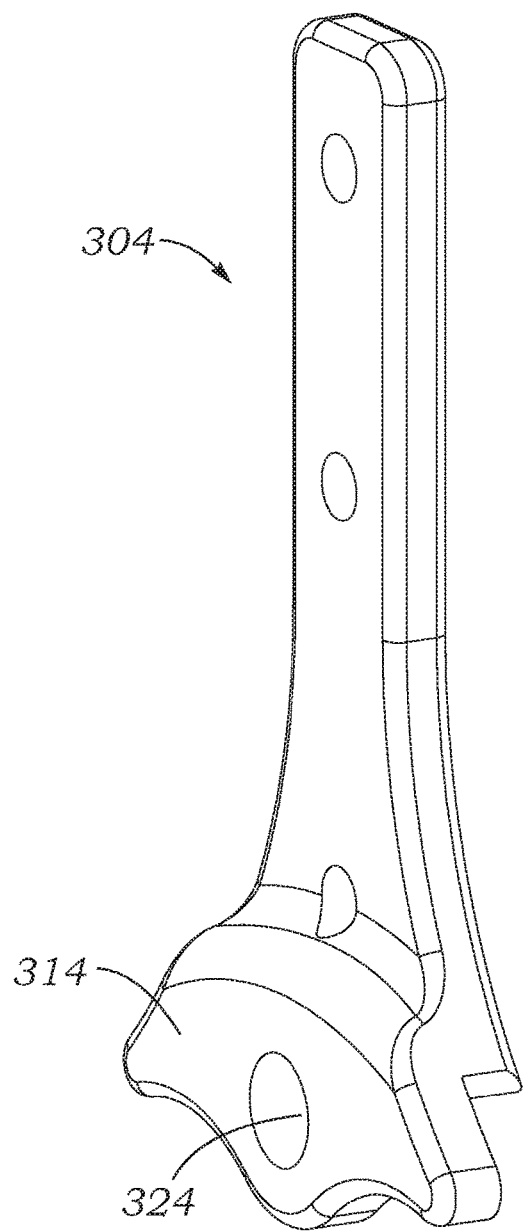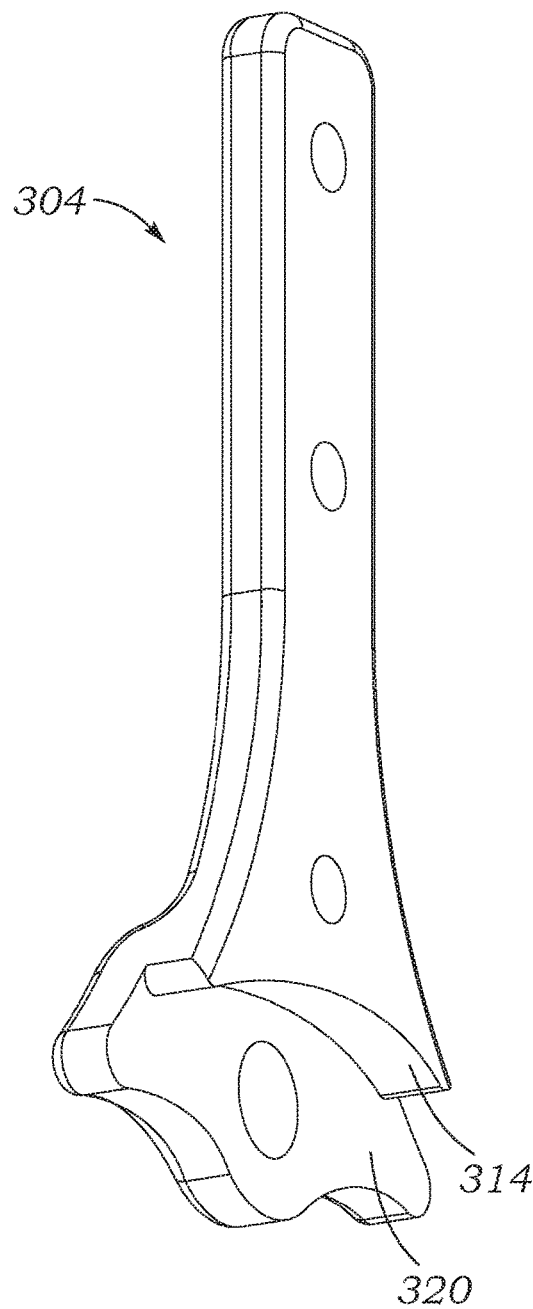
Fig. 10C
Fig. 10D

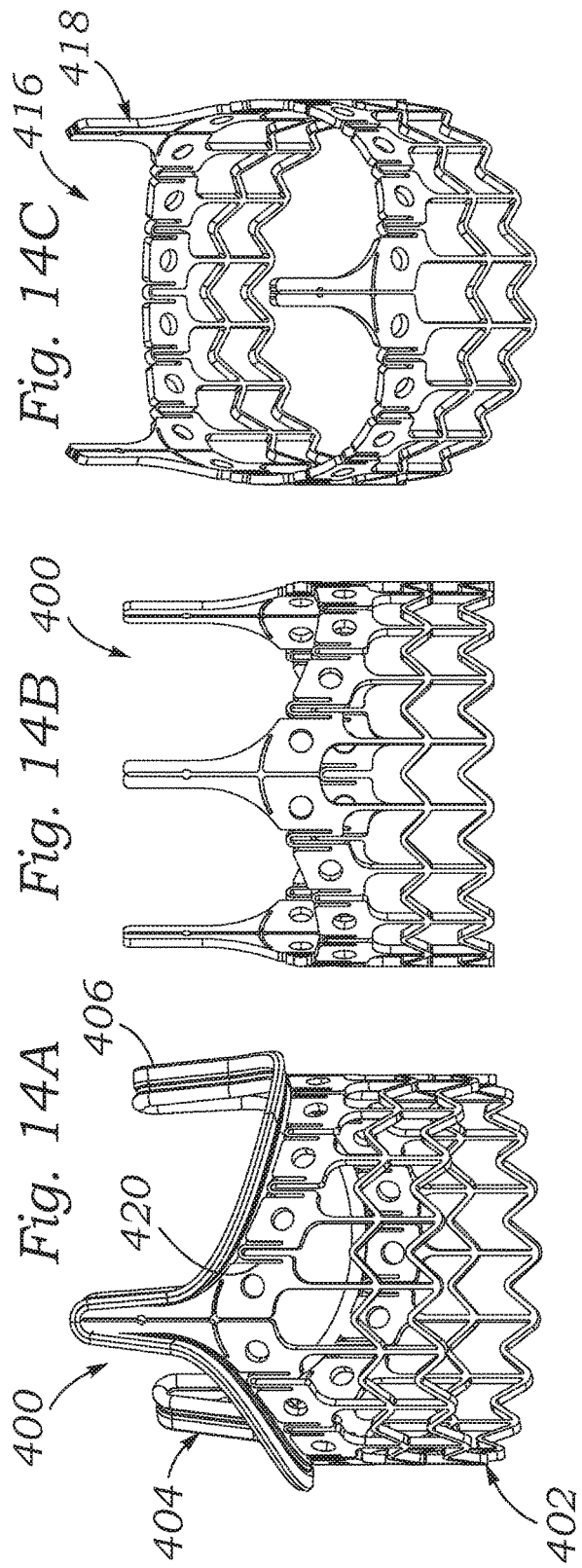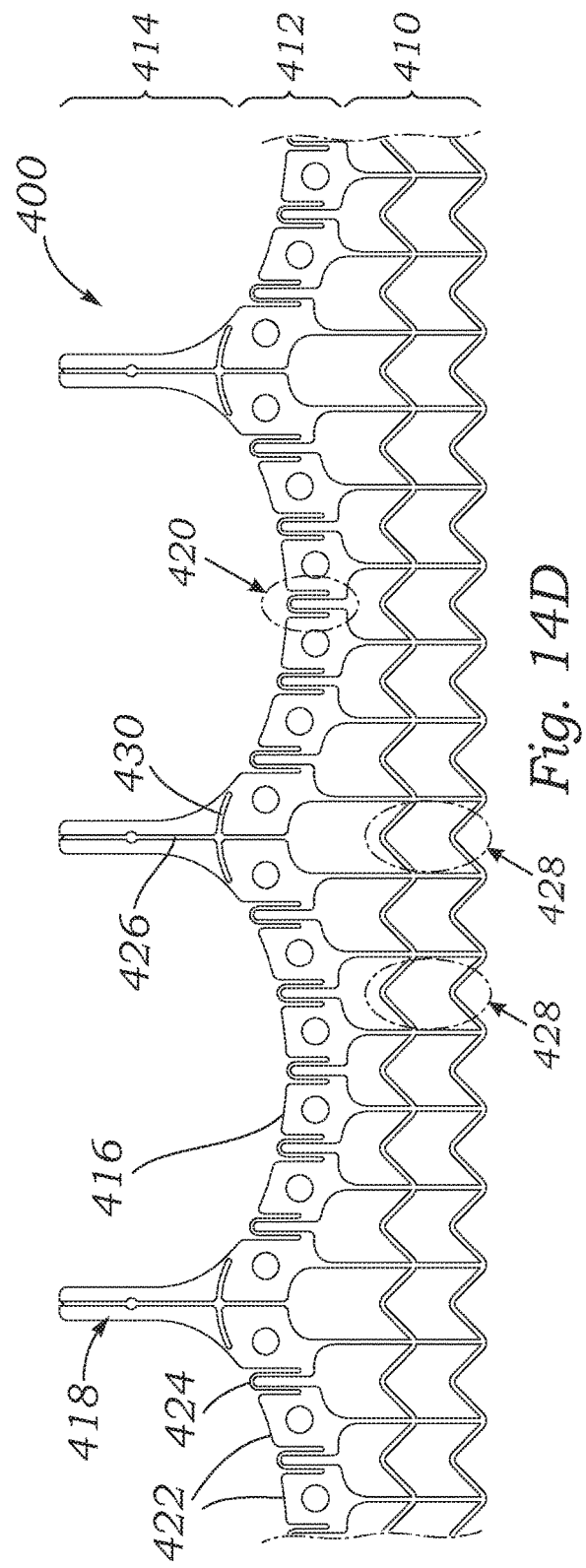

HYBRID HEART VALVES ADAPTED FOR POST-IMPLANT EXPANSION

CROSS REFERENCE TO RELATED APPLICATIONS

This application is a divisional of U.S. application Ser. No. 15/199,743, filed Jun. 30, 2016, now U.S. Pat. No. 10,695,170, which claims the benefit of U.S. Application No. 62/188,467, filed Jul. 2, 2015, the entire disclosures of which are incorporated by reference for all purposes.

TECHNICAL FIELD

The present disclosure relates to a hybrid heart valve for heart valve replacement, and more particularly to modifications to the construction of surgical heart valves to enable them to receive an expandable prosthetic heart valve therein.

BACKGROUND

The heart is a hollow muscular organ having four pumping chambers separated by four heart valves: aortic, mitral (or bicuspid), tricuspid, and pulmonary. Heart valves are comprised of a dense fibrous ring known as the annulus, and leaflets or cusps attached to the annulus.

Heart valve disease is a widespread condition in which one or more of the valves of the heart fails to function properly. In a traditional valve replacement operation, the damaged leaflets are typically excised and the annulus sculpted to receive a replacement prosthetic valve.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. The metallic or polymeric "support frame," sometimes called a "wireform" or "stent," has a plurality (typically three) of large radius cusps supporting the cusp region of the flexible leaflets (e.g., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. Components of the valve are usually assembled with one or more biocompatible fabric (e.g., polyester, for example, Dacron® polyethylene terephthalate (PET)) coverings, and a fabric-covered sewing ring is provided on the inflow end of the peripheral support structure.

Sometimes the need for complete valve replacement may arise after a patient has already had an earlier valve replacement for the same valve. For example, a prosthetic heart valve that was successfully implanted to replace a native valve may itself suffer damage and/or wear and tear many years after initially being implanted. Implanting the prosthetic heart valve directly within a previously-implanted prosthetic heart valve may be impractical, in part because the new prosthetic heart valve (including the support structure and valve assembly) will have to reside within the annulus of the previously-implanted heart valve, and traditional prosthetic heart valves may not be configured to easily receive such a valve-within-a-valve implantation in a manner that provides secure seating for the new valve while also having a large enough annulus within the new valve to support proper blood flow therethrough.

Some attention has been paid to the problem of implanting a new valve within an old valve. In particular, the following disclose various solutions for valve-in-valve systems: U.S. Patent Application Publication No. 2010/0076548, filed Sep. 19, 2008; U.S. Pat. No. 8,613,765, filed Jul. 7, 2011; and International Publication No. WO 2012/018779, filed Aug. 2, 2011. The entire disclosures of these publications are expressly incorporated herein by reference.

Despite certain advances in the valve-in-valve area, there remains a need for a prosthetic heart valve that facilitates the process while maximizing the life of the first valve and simplifying manufacturing techniques.

SUMMARY

The invention is a prosthetic heart valve configured to receive a prosthetic heart valve, such as a catheter-deployed (transcatheter) prosthetic heart valve, therein. In one embodiment, the prosthetic heart valve has a support structure that is substantially resistant to radial compression (and may be substantially resistant to radial expansion) when deployed in the patient's native heart valve annulus to replace the native heart valve (or to replace another prosthetic heart valve), but is configured to be radially expandable, and/or to transform to a generally expanded and/or expandable configuration, in order to receive a prosthetic heart valve therein, such as a percutaneously-delivered prosthetic heart valve. The transformation from expansion-resistant to expanded/expandable can be achieved by subjecting the expansion-resistant support structure to an outward force, such as a dilation force, which may be provided by a dilation balloon used to deploy a replacement prosthetic valve.

A prosthetic heart valve according to the invention may further be a "hybrid" heart valve with an additional support portion in the form of a stent frame positioned at the inflow end of the prosthetic heart valve configured to plastically expand into a substantially flared shape when subjected to a dilation force that is by itself insufficient to cause expansion of the main support structure. The stent frame is positioned upstream or on the inflow end of the entire valve portion.

A first exemplary hybrid prosthetic heart valve is adapted for post-implant expansion and has an inflow end and an outflow end. A valve member includes an inner structural support stent having upstanding commissure posts extending in the outflow direction alternating with arcuate inflow cusps. The inflow end of the valve member undulates up and down corresponding to the commissure posts and cusps. The support stent defines an implant circumference that is non-compressible in normal physiological use and has a first diameter, wherein the support stent permits expansion from the first diameter to a second diameter larger than the first diameter upon application of an outward dilatory force from within the support stent substantially larger than forces associated with normal physiological use. Also, a plurality of flexible leaflets attach along the commissure posts and inflow cusps of the support stent and ensure one-way blood flow therethrough. A plastically-expandable inflow stent frame secured to and projecting from an inflow end of the support stent has a strength requiring a predetermined expansion force to convert to an expanded state. An outflow end of the stent frame undulates with peaks and valleys to at least partially conform to the inflow end of the support stent, and wherein the outflow end has limited radially compressibility to enable compression of the stent frame during delivery of the heart valve.

The first prosthetic heart valve support stent may include a radially outer band located concentrically around and attached to a radially inner band having a single one of the expandable segments formed by overlapping free ends located at one of the cusps and separated by a sliding insert, and further including a flexible sleeve surrounding the overlapping free ends of the outer band to maintain alignment of the free ends. The single expandable segment is desirably located at one of the cusps of support the stent and the inner band is configured to expand below each of the commissure posts when the outer band expands.

A second hybrid prosthetic heart valve adapted for post-implant expansion has an inflow end and an outflow end, and a valve member including an undulating wireform with alternating cusps and commissures supporting a plurality of flexible leaflets configured to ensure one-way blood flow therethrough. A plastically-expandable inflow stent frame having a radially-expandable inflow end and an outflow end is secured to and projects from an inflow end of the wireform. The outflow end of the stent frame undulates with peaks and valleys corresponding to the wireform, and further, the outflow end includes integrated commissure posts located adjacent to and radially outward from the wireform commissures to which the leaflets attach. The outflow end defines an implant circumference with a nominal diameter that enables physiological functioning of the valve member when implanted, and the stent frame outflow end permits limited expansion from the nominal diameter to a second diameter larger than the nominal diameter upon application of an outward dilatory force from within the outflow end substantially larger than forces associated with normal physiological use.

In the second prosthetic heart valve, the stent frame is preferably configured to expand below each of the commissure posts upon application of the outward dilatory force. The integrated commissure posts may separate elements secured with sutures to the stent frame outflow end, or may be integrally formed of the same homogeneous material as the rest of the stent frame. Preferably, the stent frame includes a plurality of circumferential row struts connected by a series of spaced axial column struts, and includes an outflow row strut that extends continuously around a periphery of the stent frame having the peaks and valleys corresponding to the wireform, wherein the outflow row strut has a series of spaced V-shaped notches that permit limited expansion and contraction.

A third exemplary hybrid prosthetic heart valve adapted for post-implant expansion also has an inflow end and an outflow end and a valve member including an undulating wireform with alternating cusps and commissures supporting a plurality of flexible leaflets configured to ensure one-way blood flow therethrough. A plastically-expandable inflow stent frame having a radially-expandable inflow end and an outflow end is secured to and projects from an inflow end of the wireform. The outflow end of the stent frame undulates with peaks and valleys corresponding to the wireform, and further, the outflow end includes three commissure posts located adjacent to and radially outward from the wireform commissures to which the leaflets attach outside of the wireform. The three commissure posts are secured directly to an upper circumferential row of struts defining a nominal diameter that enables physiological functioning of the valve member when implanted. The upper circumferential row of struts is radially compressible to a smaller contracted diameter to enable compression of the outflow end during delivery of the heart valve, and the upper circumferential row of struts also is radially expandable from the nominal diameter to a larger expanded diameter upon application of an outward dilatory force from within the stent frame substantially larger than forces associated with normal physiological use.

In the third prosthetic heart valve, the stent frame is desirably configured to expand below each of the commissure posts upon application of the outward dilatory force. The stent frame may have a series of compression sections including spaces that enable a limited compression of the circumferential structure. Preferably, the upper circumferential row of struts extends continuously around a periphery of the stent frame having the peaks and valleys corresponding to the wireform, and the upper circumferential row of struts has a series of spaced V-shaped notches that permit limited expansion and contraction. Also, the upper circumferential row of struts preferably has limited radially compressibility of between about 7-20% of the nominal diameter to reduce the size of the outflow end during delivery of the heart valve.

A fourth hybrid prosthetic heart valve adapted for post-implant expansion and having an inflow end and an outflow end comprises a valve member including a plurality of flexible leaflets configured to ensure one-way blood flow therethrough and a leaflet support structure defining alternating cusps and commissures to which peripheral edges of the leaflets attach. A plastically-expandable inflow stent frame secured to and projecting from an inflow end of the leaflet support structure has a strength requiring a predetermined expansion force to convert to an expanded state. The stent frame comprising a plurality of expandable struts and an upper edge at an outflow end of the stent frame that undulates with peaks and valleys to at least partially conform to the undulating leaflet support structure. The upper edge defines an implant circumference with a nominal diameter that enables physiological functioning of the valve member when implanted, wherein the upper edge is configured to expand a limited amount from the nominal diameter to an enlarged diameter larger than the nominal diameter upon application of an outward dilatory force from within the outflow end substantially larger than forces associated with normal physiological use.

The prosthetic heart valves further may include a biodegradable band disposed concentrically and in close contact with the support stent, the biodegradable band being configured to provide resistance to expansion of the support stent after implantation, which resistance lessens over time as the band degrades in the body. Consequently, the biodegradable band is configured to provide resistance to expansion of the support stent when the predetermined expansion force is applied to the radially-expandable inflow stent.

In the various prosthetic heart valves a unique identifier may be provided on the support stent or stent frame visible from outside the body after implant that identifies the support stent or stent frame outflow end as being expandable.

Other features and advantages of the present invention will become apparent from the following detailed description, taken in conjunction with the accompanying drawings that illustrate, by way of example, the principles of the invention.

BRIEF DESCRIPTION OF THE DRAWINGS

FIG. 2 is an exploded perspective view of an exemplary prosthetic heart valve having an inner structural band combination that permits post-implant expansion, and also includes a reinforcing band that biodegrades after implant;

FIG. 3A is an elevational view of the assembled prosthetic heart valve of FIG. 2 during a step of balloon-expanding an anchoring skirt, and FIG. 3B is a sectional view through the prosthetic heart valve during a post-implantation procedure of expanding the first valve while implanting a secondary heart valve therewithin;

FIGS. 5A and 5B are perspective and elevational views of a first band for an exemplary combination of structural bands that can be used in various prosthetic heart valves to enable post-implantation expansion thereof;

FIGS. 6A-6C are perspective and enlarged views of a second band that can be coupled with the first band of FIGS. 5A and 5B to form a combination of structural bands that can be used in various prosthetic heart valve to enable post-implantation expansion thereof;

FIG. 7 is a perspective views of a combination of the structural bands in FIGS. 5 and 6 to enable post-implantation expansion of prosthetic heart valves;

FIG. 8A is a side view of a hybrid prosthetic heart valve of the present application, while FIG. 8B shows an anchoring skirt therefor with a valve member in phantom, and FIG. 8C is a perspective view of the prosthetic heart valve with portions cutaway to reveal internal structural leaflet supports;

FIG. 10A is an exploded perspective view of components of an alternative hybrid prosthetic heart valve, while FIG. 10B shows an exemplary leaflet and wireform subassembly and an anchoring skirt and commissure post subassembly for the hybrid prosthetic heart valve;

FIGS. 10C and 10D show details of separate commissure posts;

FIGS. 14A-14D are perspective, elevational, and flat plan views of an exemplary integrated frame member for use in the hybrid prosthetic heart valves disclosed herein;

DETAILED DESCRIPTION OF CERTAIN EMBODIMENTS

The prosthetic heart valves disclosed herein are "hybrid" in that they include a prosthetic valve member constructed similar to conventional surgical valves, with a relatively stable diameter that is not intended to be compressed or expanded during use after implant, and a lower expandable frame structure to help in anchoring the valve in place. Most prior valves have either a wholly non-compressible/non-expandable valve member or a wholly expandable frame structure that incorporates a valve therein. One specific commercial prosthetic heart valve that is constructed in a hybrid manner is the Edwards Intuity® valve system from Edwards Lifesciences of Irvine, Calif. The hybrid Edwards Intuity® valve system comprises a surgical non-compressible/non-expandable valve member (e.g., similar to a Carpentier-Edwards Magna Ease® valve) having bioprosthetic (e.g., bovine pericardial) leaflets coupled to a stainless steel expandable frame structure on its inflow end.

The prosthetic heart valves described herein each include an internal (meaning incorporated into the valve member itself as opposed to being a supplemental element) structural stent or frame that is generally tubular in shape and defines a flow orifice area through which blood flows from an inflow end to an outflow end. Alternatively, the shape of the internal stent can be oval, elliptical, irregular, or any other desired shape. The valves include flexible leaflets that selectively open and close to allow for one-way fluid flow therethrough.

Various internal stents disclosed herein have "expandable segments" that enable the stent to expand. This can occur from the expandable segment rupturing, plastically stretching, or elastically elongating. Thus, an "expandable segment" means a location on the stent that enables it to enlarge in diameter, such as when a balloon is inflated within the stent. Examples include weak points that can rupture, thinned areas that rupture or stretch, accordion-like structures that elongate elastically or plastically, breaks in the stent that are held together with a breakable member such as a suture or spot weld, and various other means. The term, "expandable segment" thus encompasses each and every one of these alternatives.

Figure 1A:
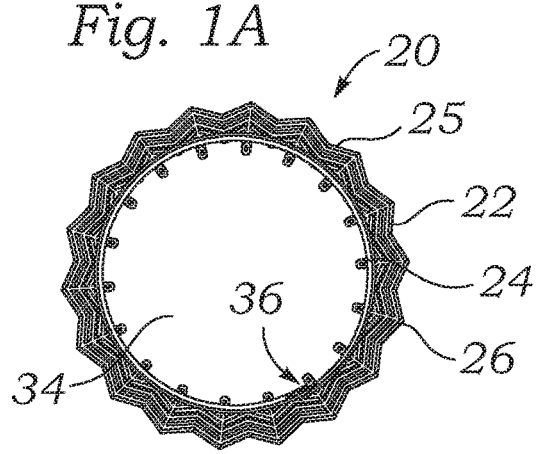
FIGS. 1A and 1B depict top and side views, respectively, of a support frame assembly for a hybrid prosthetic heart valve of the present application.
Figure 1B:
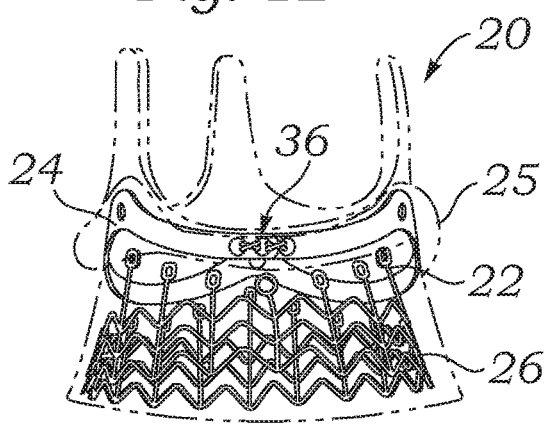
Figure 1C:
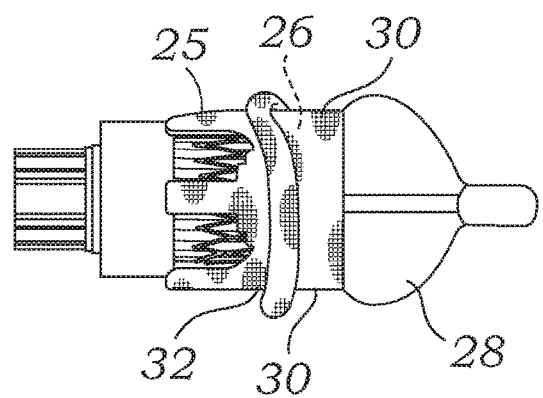
FIG. 1C is a side view of the hybrid prosthetic heart valve of FIGS. 1A and 1B, with a balloon catheter expanding the expandable skirt but not expanding the main support structure portion.
Figure 1D:
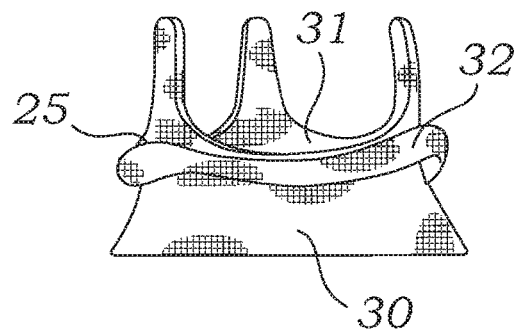
FIG. 1D shows the prosthetic heart valve after skirt expansion.
Figure 1E:
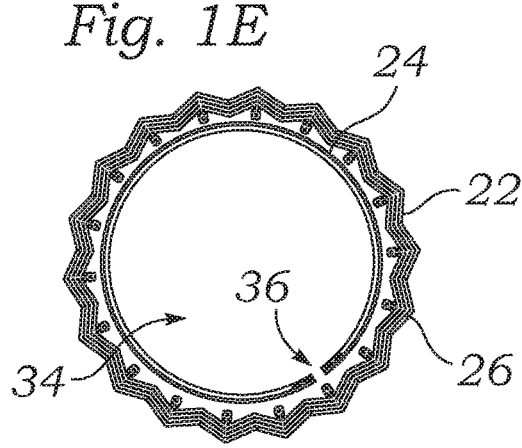
FIGS. 1E and 1F depict top and side views, respectively, of the prosthetic heart valve support structure of FIGS. 1A and 1B after a balloon catheter has radially expanded the main support structure portion into an expanded configuration.

FIGS. 1A and 1B depict an exemplary embodiment of a "hybrid" prosthetic heart valve 20, where an upper support stent 24 of a valve member 25 is joined to a lower expandable frame structure 26. The lower frame structure 26 is radially weaker than the upper support structure 24, and is configured to flare, as seen in FIG. 1B, when subjected to a radially dilating pressure such as that provided by a catheter balloon 28 such as depicted in FIG. 1C. In the embodiment depicted (and seen most clearly in FIGS. 1C-1D), the lower frame structure 26 is covered by a skirt of material 30. The prosthetic heart valve 20 includes valve leaflets (not shown for clarity) to control blood flow. The prosthetic heart valve also has a sealing or sewing ring 32 to assist in seating the prosthetic heart valve 20 in the desired location (e.g., a native valve annulus in a patient). Details on the initial deployment in a patient of the prosthetic heart valve 20 (with the upper support structure 24 in the unexpanded configuration) are set forth in U.S. Pat. No. 8,308,798, filed Dec. 10, 2009; U.S. Pat. No. 8,348,998, filed Jun. 23, 2010; and U.S. Pat. No. 8,641,757, filed Jun. 23, 2011; the contents of which are expressly incorporated herein by reference.

Figure 1F:
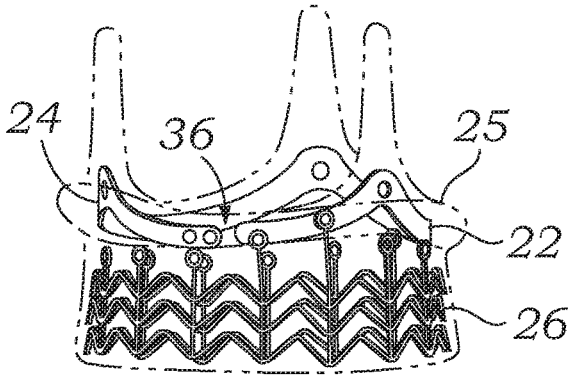

A key feature of the "hybrid" valve embodiment of FIGS. 1A-1F is that the lower frame structure 26 will flare when subjected to a dilation pressure that is insufficient to cause radial expansion of the upper support structure 24, during initial deployment of the prosthetic heart valve 20 in the patient. For instance, a catheter balloon 28 may be used to achieve the required flaring of the lower frame structure 26, while still preserving the non-expanded nature of the upper support structure 24 in order to maintain the patency of the valve leaflets, as depicted in FIGS. 1A-1B. If the prosthetic heart valve 20 should fail or otherwise need replacing in the future, a balloon catheter can be introduced into the patient, and a pressure (such as 3 atmospheres or more) sufficient to radially expand the upper support structure 24 (e.g., by causing a failure at a designed weakened area 36), which pressure is also higher than that required to flare the lower frame structure 26, may be applied to the prosthetic heart valve 20. With the resulting expansion, depicted in FIGS. 1E and 1F, the entire prosthetic heart valve 20, including the upper support structure 24 and at least an inflow end of the lower frame structure 26, are radially expanded in order to enlarge the valve orifice 34 to accommodate a new catheter-delivered prosthetic heart valve therein. Note that, post-dilation, the lower frame structure 26 may have little if any flaring, and instead has a generally constant diameter along its length, as indicated in FIG. 1F.

Note also that in another embodiment, the balloon 28 may be specially shaped (such as depicted in FIGS. 38-40 of related U.S. Pat. No. 8,641,757) so it can be positioned in such a way as to apply radially expansive pressure to the lower frame structure 26 while applying little to no radially expansive pressure to the upper support structure 24. In such an embodiment, the specially shaped balloon for radially expanding just the lower frame structure (e.g., during initial implantation of the prosthetic heart valve 20) could be positioned to apply pressure only to the lower support portion. The specially shaped balloon could then be expanded to a desired pressure, such as 4-5 atmospheres, with the pressure being applied to expand the lower support portion but not being applied to the upper support portion. At a later time when it is desired to radially expand the upper support structure (e.g., when it is desired to deploy a new valve within the existing valve), a much longer and cylindrical balloon can be used to expand both the upper and lower structures. For example, a cylindrical balloon could be positioned within both the upper and lower structures and inflated to between 4 and 5 atmospheres, thus radially expanding both the upper and the lower structures.

The "hybrid" type of prosthetic heart valve such as shown at 20 in FIGS. 1A-1F is implanted by advancing it into position at the annulus, and then inflating the balloon 28 or other mechanical expander to cause outward flaring of the lower frame structure 26. Although the upper support stent 24 is intended to remain with a constant diameter and only expand later if needed when implanting a second valve directly within, use of a traditional cylindrical balloon can inadvertently expand or distort the upper stent and possibly cause malfunction of the valve. Therefore, the present application contemplates a temporary reinforcing band to prevent any adverse effects to the upper stent from initial balloon expansion, as will be explained.

FIG. 2 is an exploded perspective view of an exemplary "hybrid" prosthetic heart valve 40 having an inner structural band combination 42 that permits post-implant expansion, and also includes a reinforcing band 44 that biodegrades after implant. The main structural components of the heart valve 40 include a plurality of flexible leaflets 50 that are connected to and supported by a continuous undulating wireframe 52, the structural band combination 42 including an inner band 54 and an outer band 56, the reinforcing band 44, and a lower frame structure 58 or anchoring skirt adapted to be expanded once implanted. Various cloth covers and interfaces are not shown for clarity, but are typically used along with sutures to hold the parts together. Again, the flexible leaflets 50 can be a combination of separate leaflets such as bovine pericardial leaflets, or a single bioprosthetic structure such as a porcine valve. The lower frame structure 58 is preferably plastically-expandable, such as being made from a suitable plastically expandable material, for example, stainless steel or cobalt-chromium alloy (e.g., Elgiloy® alloy), but may also be self-expandable in certain configurations, for example, made from nitinol.

The structural band combination 42 is desirably adapted to enable post-implant expansion, much like the embodiments described in U.S. Patent Application Publication No. 2014/0188221, filed Dec. 20, 2013, the disclosure of which is hereby expressly incorporated by reference. Indeed, the inner band 54 and outer band 56 are illustrated the same as those shown in FIGS. 6A-6B of the '221 publication, though any of the expandable band combinations can be utilized.

When the components are assembled into the valve 40, it will resemble the valve 20 shown in FIGS. 1A-1F, and also as seen in FIG. 3A that shows the valve during a step of balloon-expanding the anchoring skirt or lower frame structure 58. Once again, this is essentially the same as the heart valve in the Edwards Intuity® valve system. In addition to the modification that permits post-implant expansion, the new valve 40 features the biodegradable reinforcing band 44. The band 44 may be made sufficiently thin and shaped the same as the outer band 56 so as to be almost unnoticeable in the finished product. Furthermore, various biodegradable materials are known that are routinely included in surgical implants, and thus do not introduce any problematic materials. For example, biodegradable polymers accepted for use include polyglycolide (PGA), PGA/polylactide (PLA), polydioxanone (PDS), polycaprolactone (PCL), poly(dioxanone), and PGA/trimethylene carbonate (TMC). Consequently, the modified valve 40 includes relatively small form factor changes from the valve in the Edwards Intuity® valve system.

As mentioned, FIG. 3A illustrates the hybrid valve 40 isolated from the anatomy but shown at the moment of implantation in the annulus, such as the aortic annulus. The valve 40 is delivered on the distal end of a tubular shaft 60, such as a cannula or catheter. Although not shown, a valve holder may be utilized to couple the valve 40 to the shaft 60. An expansion member 62 such as a balloon is used to expand the anchoring skirt or lower frame structure 58 against the surrounding anatomy. For example, the frame structure 58 may be expanded to a flared shape as shown that generally conforms to the subvalvular terrain in the left ventricle, just below the aortic annulus. Again, the frame structure 58 is desirably plastically expandable, such as being made of stainless steel or cobalt-chromium alloy, and holds its flared shape. Alternatively, the frame structure 58 may be self-expandable, such as being made of nitinol, which spreads outward upon release and may apply an outward bias against the surrounding tissue. Also, the frame structure 58 may provide the sole means of holding the valve in place, or it may be supplemented with a small number of sutures, clips, or the like evenly distributed around a sealing ring 63 of the valve 40. In any event, the time of the implant process is greatly reduced from prior surgical implants by the elimination of up to 20 knot tying steps when just sutures are used.

The functional portion of the valve 40 defines an orifice diameter d that is relatively stable by virtue of the structural band combination 42, and the valve is intended to function for many years without problem. However, as mentioned, occasionally the valve 40 develops issues such as calcification, which reduces its effectiveness. This process may take decades, but eventually a re-operation to fix the valve may become necessary. The modified valve 40 is designed to enable direct expansion of a replacement valve within its orifice, the expansion widening the valve 40 without the need to explant it.

FIG. 3B thus shows a sectional view through the prosthetic heart valve 40 during a post-implantation procedure of implanting a secondary heart valve 64 therewithin. The secondary heart valve 64 is typically delivered on the distal end of a balloon catheter 66 having a balloon 68 around which a plastically-expandable stent 70 of the secondary valve is crimped. One specific valve of this type is the Sapien® valve sold by Edwards Lifesciences. If the primary valve 40 is implanted in the aortic annulus, the delivery shown is retrograde typically using a transfemoral access procedure, though an antegrade transapical procedure is also contemplated in which case the delivery catheter 66 would be shown entering the valve 40 from the opposite end. Such valves are also known as "transcatheter" valves as they typically are introduced from the end of a catheter.

The strength of the balloon 68 expansion force is sufficient to not only expand the secondary valve 64 outward into contact with the inside of the primary valve 40, but also to outwardly expand the primary valve. As mentioned with reference to FIG. 2, the reinforcing band 44 degrades over time, perhaps after 6 months to a year after implant. Consequently, the inner structural band combination 42 remains to hold the circular shape of the valve 40. Due to the expandable character of the structural band combination 42, however, the balloon 68 can cause it to outwardly expand to a larger diameter D as shown in FIG. 3B. Additionally, as stated elsewhere herein, any of the structural band configurations disclosed in the '221 publication may be utilized or modified for use as the particular structural band combination 42. Preferably the secondary valve 64 expands to have an orifice diameter that matches the original orifice diameter d of the primary valve 40, which may mean a total outward expansion of the primary valve of about 2-4 mm, equivalent to one or two valve sizes at 2-mm increments. Preferably, the flow orifice defined by the secondary valve 64 is at least equal to the flow orifice of the primary valve 40 so as to avoid any reduction of flow capacity. The plastically-expandable stent 70 is desirably robust enough to hold the primary valve 40 open despite any recoil forces generated by the valve or the surrounding annulus.

The present application discloses specific modifications to existing surgical and hybrid valves that enable manufacturers to rapidly produce a valve that accommodates valve-in-valve (ViV) procedures. Specifically, the present application contemplates retrofitting or modifying components within existing surgical valves to enable post-implant expansion. Not only does this convert any proven surgical or hybrid valve for use in a ViV procedure, but it also reduces design and manufacturing work. It is therefore necessary to describe components of one popular surgical valve to explain certain modifications thereto.

Figure 4A:
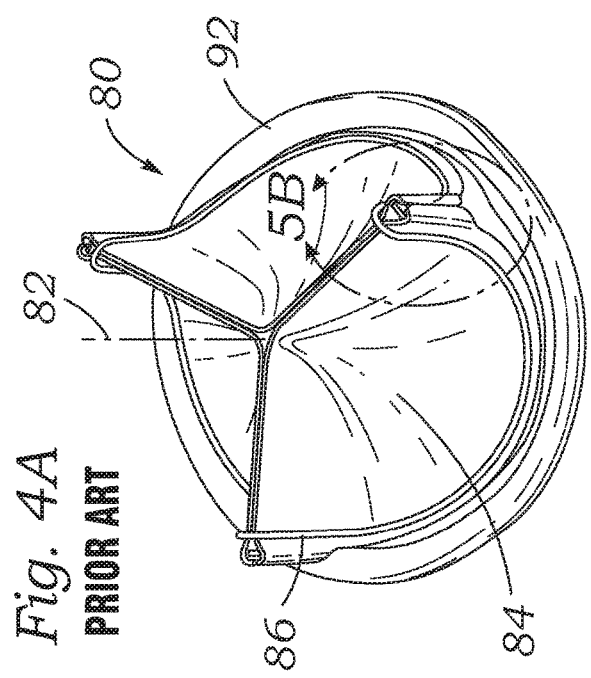
FIGS. 4A-4D are perspective and exploded views of an exemplary prosthetic heart valve of the prior art having inner structural bands.
Figure 4B:
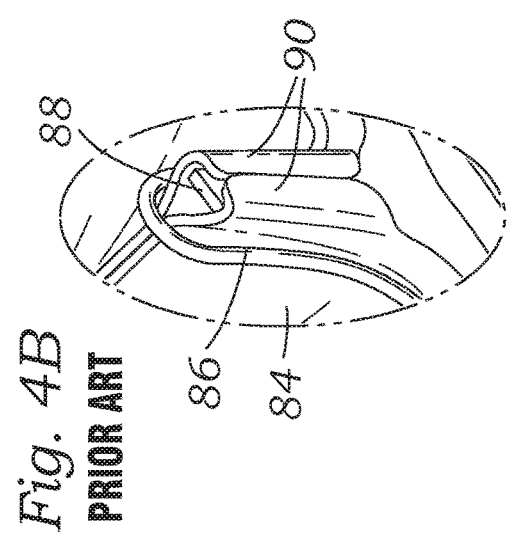

FIGS. 4A-4D are perspective and exploded views of an exemplary surgical prosthetic heart valve 80 of the prior art oriented around a flow axis 82. The heart valve 80 comprises a plurality (typically three) of flexible leaflets 84 supported partly by an undulating wireform 86 as well as by a structural stent 88. The wireform 86 may be formed from a suitably elastic metal, such as a Co—Cr—Ni alloy like Elgiloy® alloy, while the structural stent 88 may be metallic, plastic, or a combination of the two. As seen in FIG. 4B, outer tabs 90 of adjacent leaflets 84 wrap around a portion of the structural stent 88 at so-called commissures of the valve that project in an outflow direction along the flow axis 82. A soft sealing or sewing ring 92 circumscribes an inflow end of the prosthetic heart valve 80 and is typically used to secure the valve to a native annulus such as with sutures. The wireform 86 and structural stent 88 are visible in the figures, but are normally covered with a polyester fabric to facilitate assembly and reduce direct blood exposure after implant.

It should be understood that a leaflet support structure defining alternating cusps and commissures is provided for many prosthetic heart valves, and that such a support structure may or may not include a wireform. That is, some valves have a cloth-covered wireform such as shown at 86 to which the leaflets attach, as well as a structural stent 88, while in other valves a structural stent alone performs the function of the wireform. As such, the term "leaflet support structure" encompasses both variations.

Figure 4C:
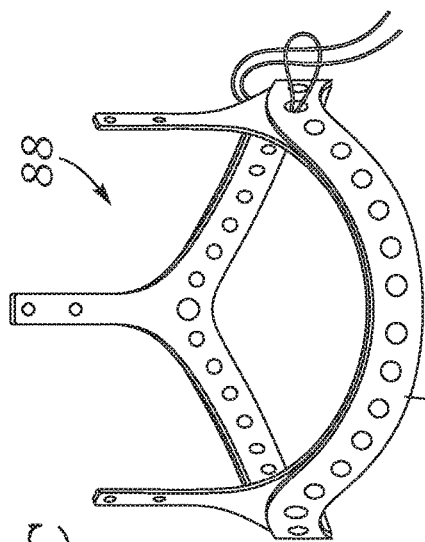
Figure 4D:
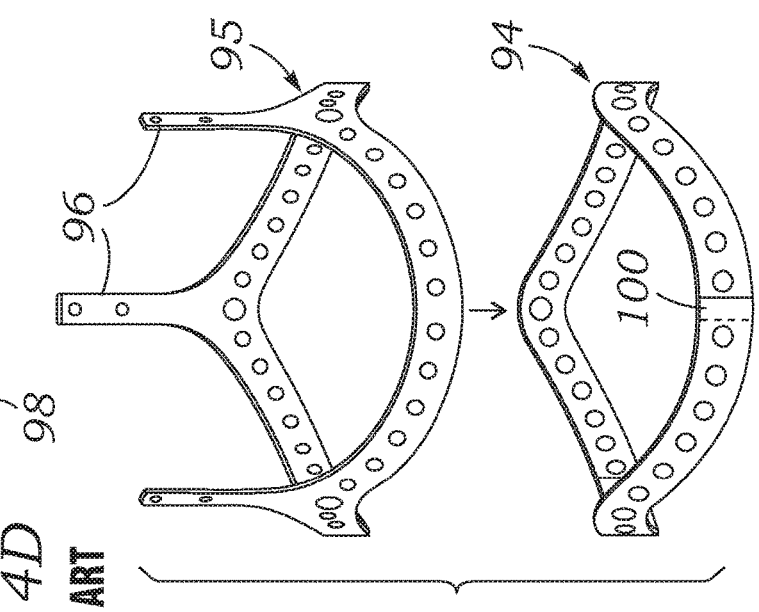

FIGS. 4C and 4D show the inner structural stent 88 in both assembled and exploded views. Although the general characteristics of the prosthetic heart valve 80 as seen in FIGS. 4A and 4B may be utilized in a number of different prosthetic heart valves, the illustrated structural stent 88 is that used in a particular heart valve; namely, pericardial heart valves manufactured by Edwards Lifesciences of Irvine, Calif. For example, the Perimount® line of heart valves that utilize pericardial leaflets 84 features an inner stent 88 much like that shown in FIGS. 4C and 4D. In particular, the stent 88 comprises an assembly or composite of two concentric bands—an outer band 94 surrounding an inner band 95. The bands 94, 95 are relatively thin in a radial dimension as compared to an axial dimension, and both have coincident lower edges that undulate axially up and down around the circumference. The outer band 94 exhibits three truncated peaks between three downwardly curved valleys, while the inner band 95 has generally the same shape but also extends upward at commissure posts 96. The downwardly curved valleys are typically termed cusps 98, as seen in FIG. 4C.

In the exemplary Perimount® valves, the outer band 94 is metallic and is formed from an elongated strip of metal bent to the generally circular shape and welded as at 100. In contrast, the outer band 95 is formed of a biocompatible polymer such as polyester (PET) or polyacetal (e.g., Delrin® polyacetal), which may be molded, and also may be formed as a strip, bent into a circular shape and welded (not shown). Both the outer and inner bands 94, 95 feature a series of through holes that register with each other so that the assembly can be sewn together, as schematically illustrated in FIG. 4C. The wireform 86 and the commissure posts 96 of the inner band 95 provide flexibility to the commissures of the valve, which helps reduce stress on the bioprosthetic material of the leaflets 84. However, the inflow end or base of the valve 80 surrounded by the sewing ring 92 comprises the relatively rigid circular portions of the structural stent 88. The combination of the metallic outer and plastic inner bands and 94, 95 presents a relatively dimensionally stable circumferential base to the valve, which is beneficial for conventional surgical use. However, the same characteristics of the structural stent 88 that provide good stability for the surgical valve resist post-implant expansion of the valve. Consequently, the present application contemplates a variety of modifications to the structural stent 88 to facilitate expansion thereof.

The exemplary prior art surgical valve 80 described above may thus be modified for post-implant expansion. Furthermore, a similar surgical valve structure is used in the aforementioned commercial Edwards Intuity® valve system, and the same modifications can be made in the valve component of that system so that it may be easily expanded post-implant. FIGS. 5-7 illustrate one such particular modification.

FIGS. 5A and 5B are perspective and elevational views of a first band 120 for use in an exemplary combination of structural bands to replace existing bands and to enable post-implantation expansion thereof. The first band 120 again has a relatively small radial thickness relative to its axial height, and includes an undulating annular shape having a dimensionally stable continuous non-compressible circumferential base defining downwardly curved cusps 122 intermediate upwardly projecting commissure posts 124. In a preferred embodiment, the first band 120 comprises a polymer material molded as a flat strip that is then bent into a circular shape and its two free ends welded as at 126.

The first band 120 includes weakened areas located below each of the commissure posts 124 that enable the band to rupture and easily expand along with the rest of the prosthetic heart valve. Such weakened areas were previously described in U.S. Patent Application Publication No. 2014/0188221, previously incorporated by reference. The first band 120 comprises a series of vertically-spaced through holes 130, 132 at each of the commissure posts 124. In particular, a first pair of through holes 130 is located closely adjacent to a lower edge 134 of the band. A vertical score line 136 through the thickness of band 120 extends vertically upwards from the first pair of through holes 130 to an upper through hole 132 that is located midway up the commissure post 124. Preferably, the score line 136 connects with the upper through hole 132. The through holes 130, 132 may be circular, as shown, or may be slightly elongated such as in a teardrop shape so as to focus any tensile forces generated from expansion of the band 120 to a certain point, such as vertically upward. Because of the relatively weak polymer material and the weakened areas provided by the through holes 130, 132 and score line 136, the first band 120 tends to split apart at three locations below the commissure posts 124. As explained, the flexible leaflets are often secured to the upper end of the commissure posts 124, which remains substantially unchanged above the upper through hole 132. Although the prosthetic heart valve in which the first band 120 is assembled is supplanted by a secondary valve, maintenance of the general integrity of the valve is desirable to avoid any loose components.

FIGS. 6A-6C are perspective and enlarged views of a second band 140 that can be coupled with the first band 120 of FIGS. 5A and 5B to form a composite structural bands for use in various prosthetic heart valve to enable post-implantation expansion thereof. In particular, the second band 140 is concentrically located around the first band 120 in intimate therewith, as seen in FIG. 7. The second band 140 also has an undulating annular shape with lower-arcuate cusp regions 142 alternating with upwardly extending commissure regions 144. The two bands differ mainly in that the commissure regions 144 of the second band 140 are truncated so that they only extend up a portion of the commissure posts 124 of the first band 120.

The second band 140 is desirably metallic, such as a Co—Cr—Ni alloy like Elgiloy® alloy, and preferably formed initially as a flat band that is bent into an annular shape and has two free ends 146*a*, 146*b* that overlap and engage each other for expansion. One preferred example of such engagement is shown in FIGS. 6B and 6C. Other examples of overlapping free ends that permit post-implant expansion are shown and described in U.S. Patent Application Publication No. 2014/0188221.

In the illustrated embodiment, the two free ends 146*a*, 146*b* are each distinguished from the rest of the band at a pair of shoulders 148 that reduce the axial height of an intermediate portion 150 having a central circumferential slot 152. Each free end 146*a*, 146*b* terminates in an axially enlarged head 154 (or oppositely-directed axial bumps) having an axially height that is approximately the same as the majority of the band 140. A sliding insert 156 or "spacer" is interposed between the two free ends 146*a*, 146*b* to reduce sliding friction between. For example, the insert 156 is formed of a lubricious material such as polyester. The insert 156 has a shape that somewhat mirrors the combination of the two free ends 146*a*, 146*b*; namely, having an axial height approximately the same as the intermediate portion 150, a central circumferential slot, and axial protrusions the same size as the enlarged heads 154. The polyester insert 156 between the two metal band ends 146*a*, 146*b* also prevents metal-on-metal fretting during normal cardiac cycling, which may cause slight relative motion.

The assembly of the two free ends 146*a*, 146*b* and insert 156 is seen in FIG. 6B, and is held together by a flexible sleeve 158 that surrounds the free ends 146*a*, 146*b* and holds them radially together. The sleeve 158 desirably comprises polyester (e.g., PET) shrink wrap tubing, or may be an elastomeric material, such as silicone rubber, and is shown transparent to illustrate the mating free ends 146*a*, 146*b*. The two free ends 146*a*, 146*b* may slide apart a predetermined distance while still being overlapping. The flexible sleeve 158 provides a minimum amount of friction against the axially enlarged heads 154 but generally just serves to maintain alignment of the free ends 146*a*, 146*b*. The flexible sleeve 158 nominally maintains the diameter of the band so that it is stable during manufacturing, but allows it to easily open up once a valve-in-valve procedure is performed.

Each of the free ends 146*a*, 146*b* further includes the circumferentially-oriented slot 152 that stops short of the terminal ends 154 and provides a pathway for fluid flow. Preferably, slots 152 extend farther outward from the sleeve 158 so that fluid can always enter the space within the sleeve. During storage, the slots 152 permit flow of a fluid between the overlapping free ends 146*a*, 146*b* to allow for sterilization. Moreover, the sleeve 158 may be biodegradable to maintain alignment of the two free ends 146*a*, 146*b* for a period after implant and then degrades to permit even easier expansion of the band 140.

The band 140 shows a still further identifying trait visible using external imaging and signifying it is expandable. In the illustrated embodiment, a pattern of three holes 160 are provided at each commissure region 144. Again, this permits a surgeon contemplating a replacement operation to quickly confirm that a valve-in-valve procedure is a possibility. The band 140 may also include a valve size indicator visible using external imaging, as illustrated below with respect to FIGS. 8-9, and as detailed in U.S. application Ser. No.

14/745,287, filed Jun. 22, 2015, now U.S. Pat. No. 9,504, 566, the contents of which are hereby expressly incorporated by reference.

The assembly of the first band 120 in intimate contact with the second band 140, as seen in FIG. 7, provides good stability for the prosthetic valve leaflets when in use, having a dimensionally stable continuous circumferential base defining an implant circumference with a first diameter that is non-compressible in normal physiological use, and an advantageous expandable structure if and when a valve-in-valve procedure is necessary. The preferably metal outer band 140 only expands at one location, while the preferably polymer band 120 expands at all three commissures. The outer band 140 is able to slide within the surrounding cloth coverings and relative to the other components such that the valve expands generally uniformly around its perimeter. That is, the commissure areas of a wireform to which the leaflets attach (such as at 52 in FIG. 2) and commissure areas of the metal band 140 are initially aligned, or registered. As the metal band 140 expands, the registered commissure areas become misaligned since the wireform expands at all three commissures and the metal band only expands at the one cusp. However, the valve becomes obsolete, having been replaced with a transcatheter valve, and so this misalignment is of no consequence. The wireform maintains the upstanding commissure posts of the expanded valve in roughly the same location as when they were functional, which is intermediate the surrounding coronary ostia, and thus valve expansion will not end up blocking critical blood flow to the coronary arteries.

FIGS. 8A-8C illustrate a hybrid prosthetic heart valve 170 of the present application, which includes an upper valve member 172 coupled to a cloth-covered anchoring skirt 174. FIG. 8B shows the valve member 172 in phantom to illustrate the contours of an expandable frame 176 of the anchoring skirt 174, and FIG. 8C is a perspective view of the entire heart valve 170 with portions at one commissure post 178 cutaway to reveal internal structural leaflet supports.

The valve member 172 of the hybrid prosthetic heart valve 170 shares some structural aspects with the prior art heart valve 80 illustrated in FIGS. 4A-4D. In particular, an internal support frame defines three upstanding commissure posts 178 alternating with three arcuate cusps 180 curving in an inflow direction. Three flexible leaflets 182 are supported by the commissure posts 178 and cusps 180 and extend across a generally cylindrical flow orifice defined within the support frame. An undulating typically metallic wireform 184 mimics the up and down shape of the support frame and the leaflets 182 are attached to the wireform via a cloth covering. As with earlier valve constructions, an internal stent band 186 includes upstanding posts that rise up adjacent to and just outside of the commissures of the wireform 184, and outer tabs 188 of the leaflets 182 extend underneath the wireform, wrap around the stent posts, and are secured thereto with sutures.

In the illustrated embodiment, the heart valve 170 also includes a highly compliant sealing ring 190 extending outward therefrom at approximately the interface between the valve member was 172 and the anchoring 174. The sealing ring 190 as well as the expandable frame 176 are covered with a fabric 192 that helps prevent leakage around the outside of the valve once implanted. Furthermore, the sealing ring 190 is also suture-permeable and may be used to secure the valve in place in the native annulus.

Figure 9A:
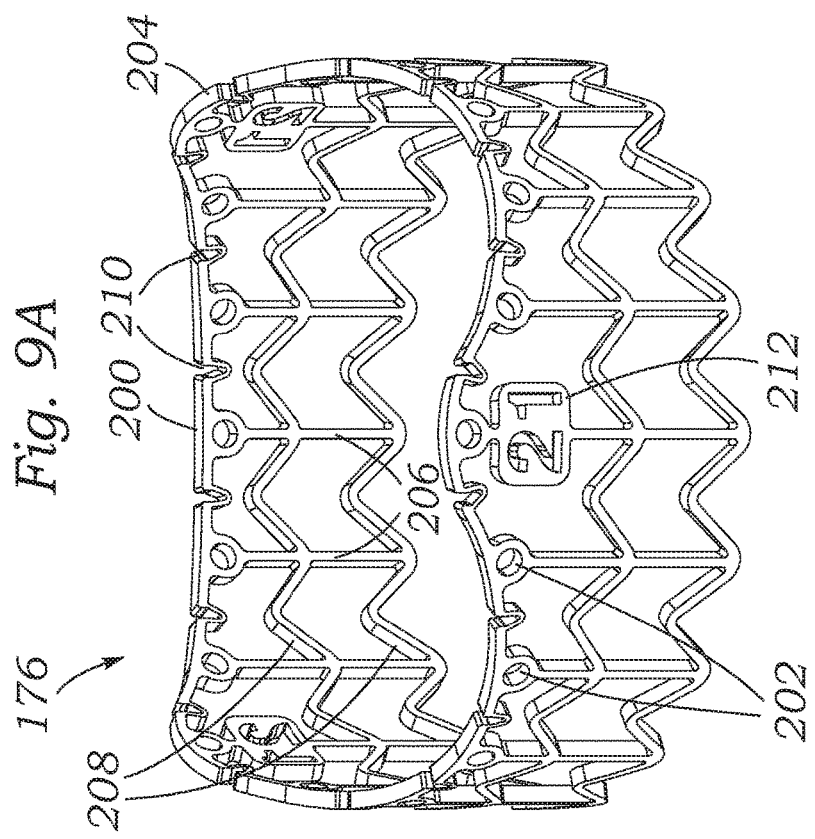
FIGS. 9A-9C are perspective views of an exemplary anchoring skirt for use in the hybrid prosthetic heart valve of FIGS. 8A-8C.
Figure 9B:
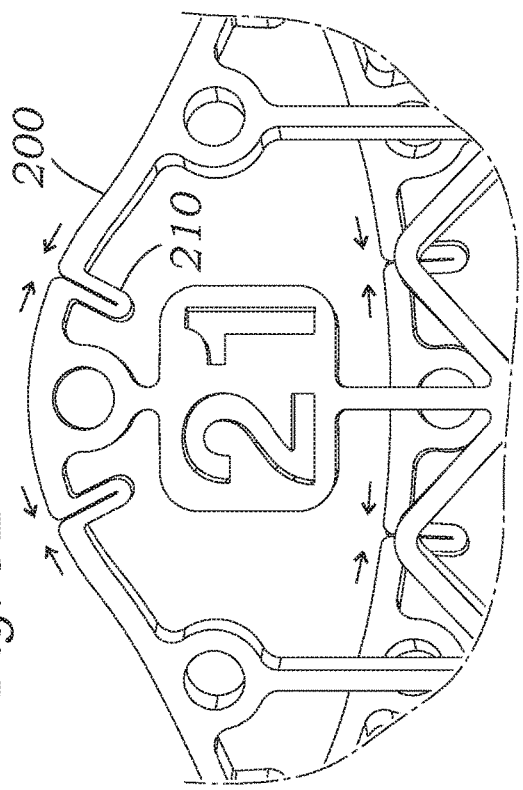
Figure 9C:
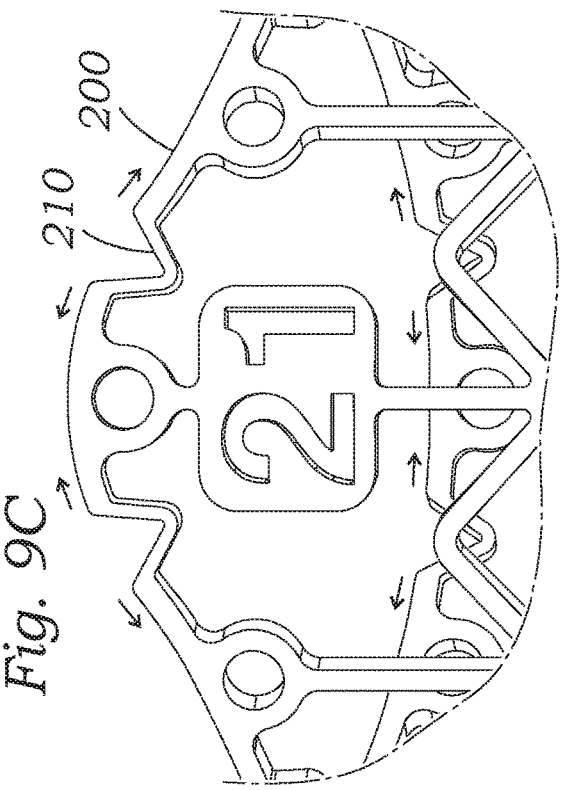

FIGS. 9A-9C illustrate details of the exemplary expandable frame 176 for use in the hybrid prosthetic heart valve 170 of FIGS. 8A-8C.

Figure 16:
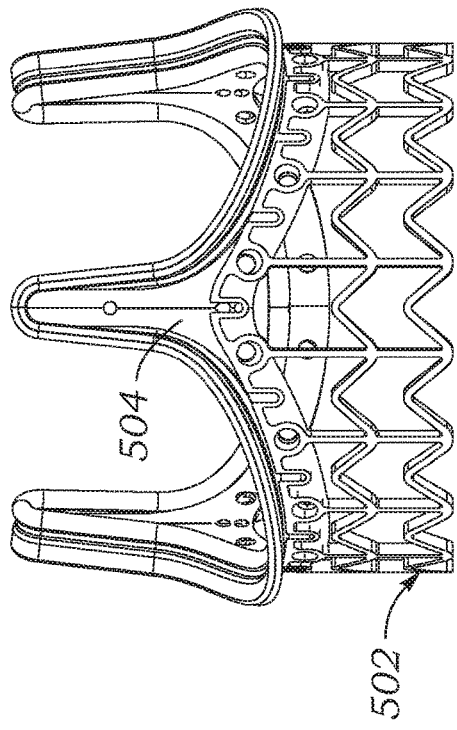
FIG. 16 is a perspective view of an alternative integrated frame member having an expandable frame connected to a polymer band that forms commissure posts.

With specific reference to FIG. 16, the lower frame 176 is shown in perspective and includes a plurality of circumferential row struts connected by a series of spaced axial column struts. Specifically, an upper or outflow row strut 200 extends continuously around a periphery of the frame 176, and preferably follows a gently undulating path so as to match a similar shape of the underside of the upper valve member 172 (FIG. 8B). As seen in FIG. 9A, three peaks 204 along the upper row strut 200 correspond to the locations of the commissures 178 of the valve 170, where the lower edge of the stent band 186 rises upward as well. In general, the lower frame 176 attaches to an inflow end of the upper valve member 172, and preferably directly to or to fabric covering the internal support frame. The lower frame 176 is initially generally tubular and expands to be somewhat conical with the free end farthest from the upper valve member 172 expanding outward but the end closest remaining the same diameter.

The upper row strut 200 includes a plurality of eyeholes 202 evenly spaced apart and located just below the top edge thereof that are useful for securing the frame 176 to the fabric of the underside of the valve member 172. A series of axial column struts 206 depend downward from the upper row strut 200, and specifically from each of the eyeholes 202, and connect the upper row strut to two lower row struts 208. The lower row struts 208 circumscribe the frame 176 in zig-zag patterns, with an inverted "V" shape between each two adjacent column struts 206. The lower row struts 208 preferably traverse horizontally around the frame, and the length of the column struts 206 thus varies with the undulating upper row strut 200.

As mentioned above, the lower frame 176, in particular the inflow end thereof, may be plastically expanded, such as by balloon expansion, and may be formed of stainless steel, for example. In a conventional Edwards Intuity® valve, the upper row strut 200 is generally ring-like without capacity for compression or expansion. In the illustrated frame 176, on the other hand, a series of spaced notches 210 are provided that permit expansion and contraction. That is, circumferential segments of the strut 250 are interrupted by the V-shaped notches 210, which permit a limited amount of expansion, perhaps about 3 mm in diameter, to accommodate a supplemental expandable valve to be inserted and expanded therein. More particularly, the upper row strut 200 (outflow end) of the frame 176 defines a nominal diameter seen in FIG. 9A that enables functioning of the valve member 172. The upper row strut 200 is radially compressible from the nominal diameter to a smaller contracted diameter to enable compression of the outflow end of the frame 176 during delivery of the heart valve. The upper row strut 200 is also radially expandable from the nominal diameter to a larger expanded diameter upon application of an outward dilatory force from within the stent frame such as in a valve-in-valve procedure.

As shown in FIG. 9B, the modified frame 176 can be collapsed to a pre-determined minimum diameter for delivery and expanded to a pre-determined maximum diameter during a valve-in-valve procedure. More specifically, the upper row strut 200 of the illustrated frame 176 may be collapsed by about 2 mm relative to the nominal diameter for ease of delivery by compressing the V-shaped notches 210 as indicated. Because the notches 210 can only be compressed until the two corners meet, the frame 176 can only be collapsed by a predetermined amount. The exemplary frame 176 is specifically designed to be collapsible to ease insertion through small incisions when the valve is implanted and for ease of seating in the annulus. The amount of collapse could be as large as about 40-50% by diameter, but would more preferably be about 2-3 mm, or between about 7-20% for heart valves having nominal operating diameters between about 19-29 mm. A compression of 2 mm in diameter, for example, corresponds to a change in circumference of about 6.28 mm. The stent frame is divided into 18 segments around its circumference by the axial column struts 206. Therefore, by placing an initial gap of 0.35 mm (6.28 mm/18) in each segment, the frame can collapse by about 2 mm in diameter before adjacent segments make contact and hence prevent further compression.

FIG. 9C discloses that the upper row strut 200 of the illustrated frame 176 may be subsequently expanded by 3 mm relative to a nominal diameter during a valve-in-valve procedure. Because of the configuration of the upper row of struts, the outflow portion of the frame cannot be expanded more than 3 mm. That is, the V-shaped notches 210 eventually straighten out, which prevent further expansion. Desirably, the frame is designed to expand about 3 mm in diameter beyond its nominal diameter. The nominal diameter is defined when the notches 210 are V-shaped, prior to either contraction or expansion. Similar to the gaps for limiting compression, the 3 mm in expansion corresponds to a 9.42 mm (3 mm×π) change in circumference. Therefore, each of the 18 segments must limit expansion to 9.42 mm/18=0.52 mm. The length of the "V" shaped struts connecting each segment are thus 0.52 mm+0.35 mm (from the compression gaps)=0.87 mm. During a valve-in-valve expansion, the expansion of the stent frame would be limited by the expansion-limiting struts at the point where they became straight across the gap between adjacent frame segments.

If it was not desired to have the frame collapsible but expansion was still desired, the gaps could be reduced to about 25 μm, the practical limit of laser cutting. With 18 gaps of 25 μm, the amount of compression would only be (18×25 μm/π)=0.143 mm (about 0.006").

In contrast, earlier designs simply removed the upper row of struts that defines the outflow diameter of the frame. That frame configuration had no way to limit the maximum expansion of the valve during a valve-in-valve procedure. Additionally, there could be an advantage to having hybrid valves that are collapsible by a limited amount (e.g., about 2-3 mm) for easier insertion. While a frame without an upper row of struts could be collapsed, there is no limit the amount of compression. It might be desirable to have the maximum compression amount limited as disclosed here for consistency and for preventing physicians from trying to collapse the valve more than it can safely be collapsed.

In addition, a number of valve type indicators 212 are integrated into the frame 176 at locations around its circumference, such as three valve size indicators. In the illustrated embodiment, the valve size indicators 212 comprise small plate-like tags inscribed with the numerical valve size in mm, for example 21 mm in the illustrated embodiment. The use of any alphanumeric characters or other symbols that signify size or other feature of the valve are contemplated. The stainless steel frame 176 may be laser cut from a tubular blank, with the plate-like size indicators 212 left connected to one more of the struts. As shown, the size indicators 212 are located just below the peaks 204 of the undulating upper row strut 200, connected between the corresponding eyehole 252 and the descending column strut 206. There are thus three size indicators 212 spaced 120° apart around the frame 176. This location provides additional space between the upper row strut 200 and the adjacent lower row strut 208. Further, the frame 176 typically has more real estate in which to place the size indicators 212 than the bands of the valve member 172. The inscribed or cutout valve size numerals are sufficiently large to be visualized with X-ray, transesophageal echocardiography (TEE), or other imaging modality. In one embodiment, the valve size numerals are from about 1.5 mm to about 2 mm in height, for example, about 1.75 mm in height.

FIG. 10A is an exploded perspective view of components of an alternative hybrid prosthetic heart valve 300. The alternative heart valve 300 does away with an internal stent or support frame previously shown as the composite bands 120, 140 in FIG. 7, for example. The composite band structure was the primary source of circumferential rigidity to the heart valves in which they were employed, and thus expansion structure was necessary to enable valve-in-valve procedures. The alternative hybrid heart valve 300 includes a lower compressible/expandable frame 302, as before, separate commissure posts 304 that are secured to the frame, and an undulating wireform 306 supporting flexible leaflets 308, also as before.

FIG. 10B shows a subassembly 310 including the wireform 306 juxtaposed with the three leaflets 308, and an "integrated" subassembly 312 of the expandable frame 302 with the commissure posts 304 attached thereto. Each of the flexible leaflets 308 has two tabs 309, and pairs of tabs on adjacent leaflets are shown projecting through (under) the inverted V-shaped commissures of the wireform 306. These pairs of tabs 309 then wrap around one of the upstanding commissure posts 304 of the subassembly 312, which are located adjacent to and radially outward from the wireform commissures. The subassemblies 310, 312 are eventually covered with biocompatible fabric such as polyester, and the pairs of tabs 309 and commissure posts 304 are secured to each other with a cloth covering (see FIG. 13).

Due to the attachment of the commissure posts 304 to the frame 302 the subassembly 312 integrates the frame and commissure posts, while as described below, an "integrated" frame may mean that the commissure posts are integrally formed of the same homogeneous material as the rest of the stent frame. Integrated in this sense meaning the two components are securely attached together prior to assembly with the wireform/leaflet subassembly 310, either by securing the two parts or forming them at the same time from the same material. Furthermore, a hybrid heart valve with an "integrated" frame means that the frame provides both the expandable skirt frame as well as commissure posts to which the leaflets attach, without any additional structural bands, such as the metal band 94 seen in FIG. 1A. With this configuration, the number of parts in the valve is reduced, which reduces assembly time and expense.

FIGS. 10C and 10D illustrate a commissure post 304 from an outer and an inner perspective, respectively. A lower end of each of the commissure posts 304 includes a concave ledge 314 that matches the contour of one of the peaks 316 in the undulating upper row of struts 318 of the expandable frame. As seen in FIG. 10B, an outer plate 320 below each of the concave ledges 314 of the commissure posts 304 extends downward on the outside of the expandable frame 302. Sutures 322 secure the commissure posts 304 to the frame 302 via suture holes 324 that align with eyeholes 326 at the peaks 316 of the undulating upper row strut 318. This shape matching followed by covering with fabric provides a relatively stable arrangement of the commissure posts 304 in the integrated frame subassembly 312.

Figure 11:
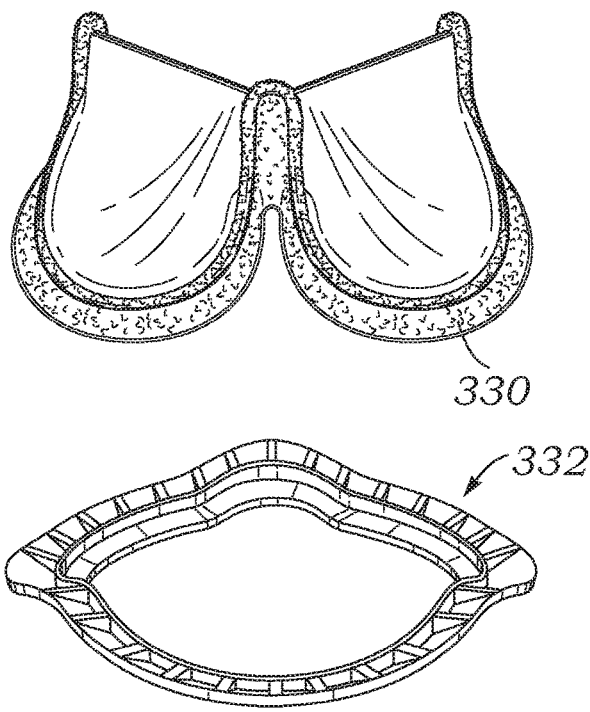
FIG. 11 is another exploded perspective view of subassemblies of the alternative hybrid prosthetic heart valve.

FIG. 11 is another exploded perspective view of subassemblies of the alternative hybrid prosthetic heart valve 300. In this view, the wireform in the subassembly 310 of the wireform and leaflets has been covered with fabric, and features an outwardly projecting flap 330. The fabric flap 330 is used to secure the wireform/leaflet subassembly 310 to the subassembly 312 of the expandable frame 302 and commissure posts 304. Furthermore, a suture-permeable sealing ring 332 may be attached such as by sewing at the juxtaposition between the two subassemblies 310, 312.

Figure 12:
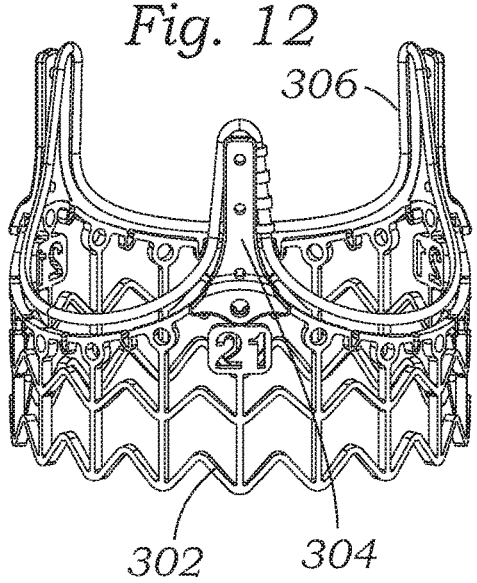
FIG. 12 shows the relative positions of the anchoring skirt and commissure post subassembly and wireform for the alternative hybrid prosthetic heart valve.
Figure 13:
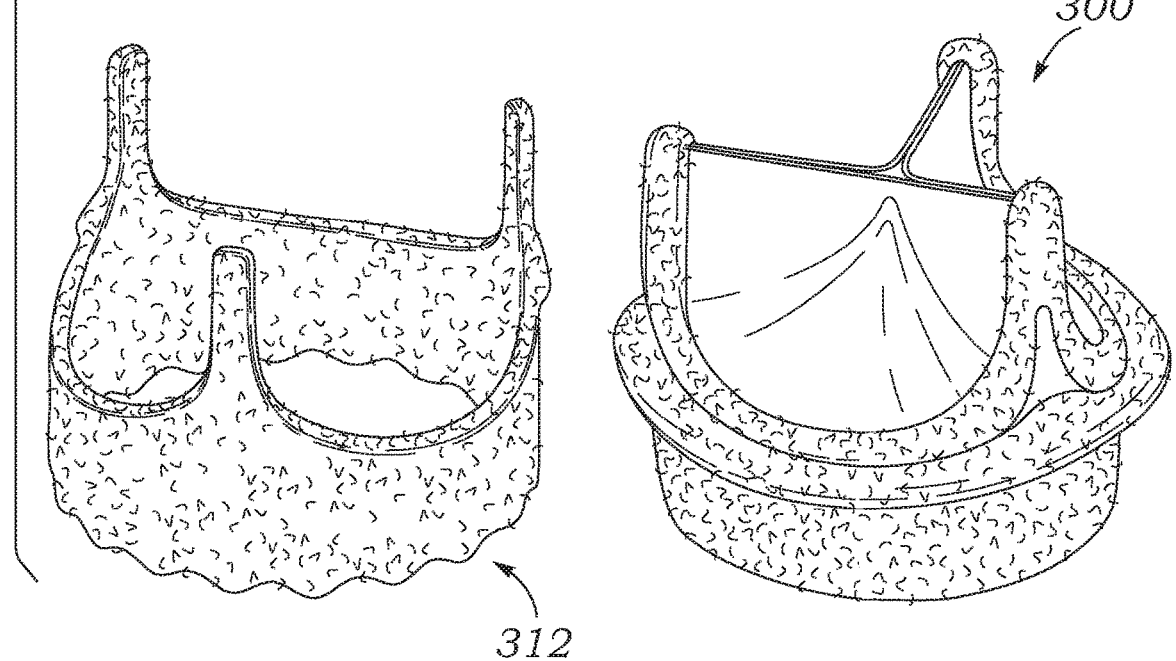
FIG. 13 is a perspective view of the finished hybrid prosthetic heart valve.

The relative positions of the wireform 306 and the frame/commissure post subassembly 312 is seen in FIG. 12, and also in further detail in FIGS. 12A-12D, with the commissure posts 304 immediately outside of the commissures of the wireform 306. Finally, FIG. 13 is a perspective view of the finished hybrid prosthetic heart valve 300 entirely covered with fabric.

The removal of the aforementioned stent bands and attachment (integration) of the commissure posts 304 directly to the frame 302 greatly simplifies construction, reduces labor hours, lowers the radial profile of the valve by about 1.6 mm, and allows for expansion during a valve-in-valve procedure. A preferred construction sequence involves attaching the sealing ring 332 to the expandable frame 302, along with 3 cloth-covered commissure posts 304, then attaching this assembly to the wireform/leaflet subassembly 310 during final assembly.

The commissure posts 304 disclosed have specific features that interface with the frame 304 to add stability to the posts in all directions. That is, the specific surfaces 314, 320 that mate with the corresponding peaks 316 on the frame 302 as well as the holes 324 that allow the posts to attach with sutures 322 to the frame provide excellent stability in all directions for subsequent covering with fabric. The commissure posts 304 could be molded from polyester or some other biocompatible material into the shape shown here, or even produced using 3D printing.

FIGS. 14-18 illustrate alternative integrated anchoring skirt and commissure post subassemblies. As described above with respect to FIGS. 10-13, the subassembly 312 shown in FIG. 10B eliminates the need for annular structural bands, which bands provide stability and rigidity but which impede the ability of the valve to expand post-implant. Each of the alternative subassemblies shown in FIGS. 14-18 also eliminate the need for the structural bands, and further integrate the anchoring skirt and the commissure posts.

FIG. 14A shows an assembly 400 of the structural components of a hybrid prosthetic heart valve having an integrated frame member 402 much like those described above but formed of a single piece. A schematic wireform 404 is shown situated on top of the frame member 402 in FIG. 14A, with flexible leaflets and a cloth cover not shown and representing a wireform/leaflet subassembly such as shown at 310 in FIG. 11. The schematic wireform 404 is shown with an outwardly extending sewing flange 406, which may be formed by joined lengths of two fabric tabs that wrap around and cover the wireform. When covered with cloth, the frame member 402 serves as the supportive component for the wireform, leaflets and sealing ring. Further, when covered with cloth, the frame member 402 provides an effective seal against paravalvular leaking (PVL) and circumferential stability to the valve.

The integrated frame member 402, which is also shown in FIGS. 14B-14D, comprises a lower expandable skirt portion 410, an upper annulus band 412, and leaflet support posts 414. The skirt portion 410 comprises a number of chevron patterned or V-shaped struts that can be easily crimped and then expanded. The annulus band 412 provides real estate for the attachment of a sealing ring (not shown), and preferably includes a series of holes around its circumference through which to pass sutures connecting the sealing ring. The integrated frame member 402 includes multiple cuts that enable post-implant expansion and may be laser-cut from a suitable metal such as cobalt-chromium alloy (e.g., Elgiloy® alloy) and electropolished.

The frame member 402 is desirably formed from a tubular blank of a suitable material, and has a generally circular inflow or lower edge and an undulating outflow or upper edge. More particularly, the upper edge defines three arcuate cusp portions 416 intermediate three upstanding commissure posts 418. The undulating upper edge is shaped to closely fit underneath the wireform 406. After assembling the frame member 402 with the rest of the heart valve components, the skirt portion 410 is typically crimped in a generally conical manner such that its lower edge has a smaller diameter than its upper edge.

Compression/expansion sections 420 along the annulus band 412 are also added to enable a limited collapse of the frame member 402 during delivery. The compression/expansion sections 420 comprise slits formed in the upper edge of the frame member 402 that have spaces enabling a limited compression, and also permit expansion. In a preferred embodiment, solid segments 422 spaced around the annulus band 412 are connected by thin inverted U-shaped bridges 424.

As seen in FIG. 14D, the frame member 402 further includes a number of slits in the region of the commissures 418 to facilitate expansion and general flexibility of the frame member. An elongated central slit 426 extends nearly the entire height of each of the commissures 418. Regions of expandable circumferential struts 428 are positioned within the skirt portion 410 axially aligned with both the compression/expansion sections 420 and the central slits 426. When an outward radial force is applied from within the heart valve having the frame member 402, the annulus band 412 permits expansion because of both the sections 420 and slits 426. Additionally, short arcuate slits 430 are formed at the base of each of the commissure posts 418, generally following a truncated undulating line joining the cusp portions 416. These slits 430 reduce the radial stiffness of the posts 418 such that most of the physiological load absorbed by the flexible leaflets is transferred to the wireform 406, rather than to the posts.

Despite the arcuate slits 430 in the frame member 402 of FIGS. 14A-14D, there are concerns that such an integrated frame design will stiffen the wireform commissure post area, thus altering the load carry mechanism of proven commercial valve platforms. To alleviate such concerns, the three commissure posts may be made of three separate pieces, preferably using polymeric material, such that when connected with the underlining metal frame with sutures, there will not be metal to metal contact.

Figure 15A:
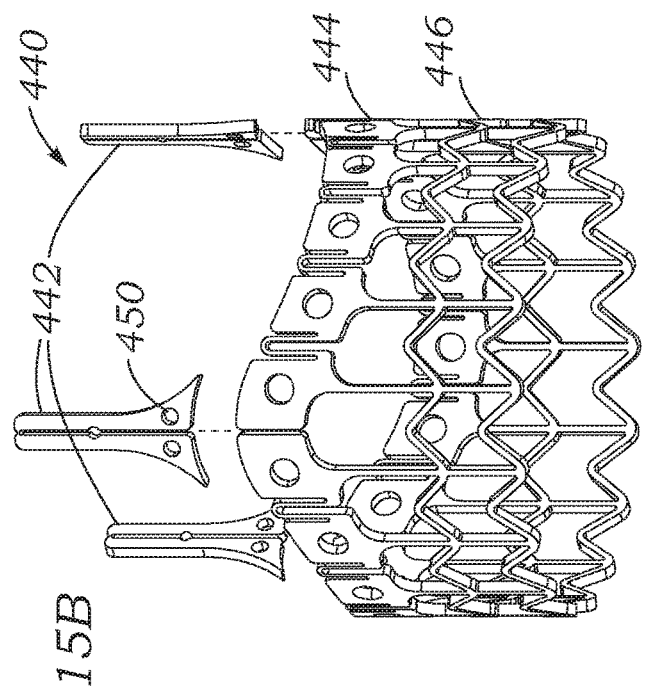
FIGS. 15A-15D are several views of an alternative integrated frame member much like that shown in FIGS. 14A-14D but with commissure posts that are separated from a lower expandable frame.
Figure 15B:
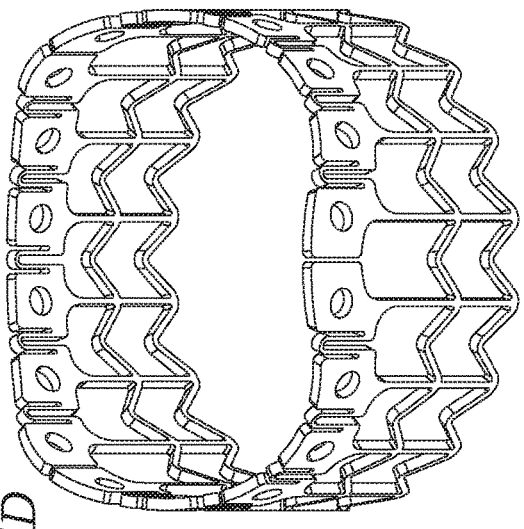
Figure 15C:
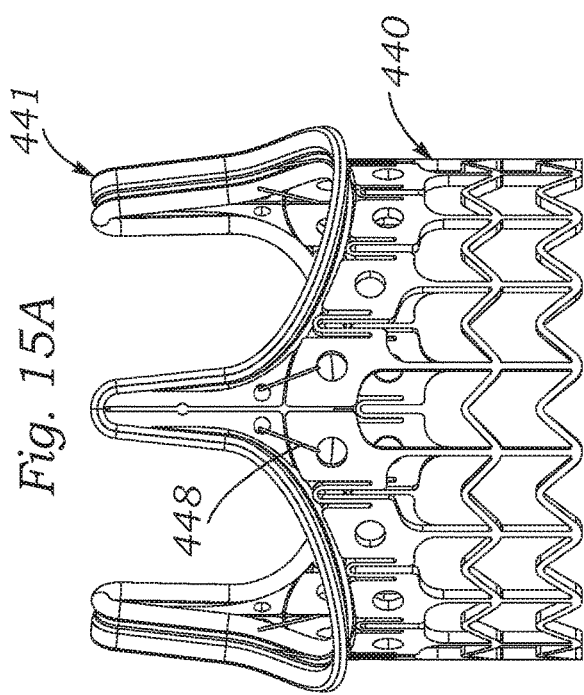
Figure 15D:
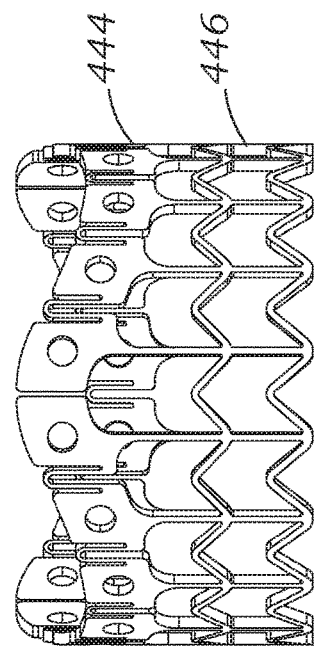

For instance, FIGS. 15A-15D illustrate an alternative frame member 440 that is configured about the same as the frame member 402, but has separate commissure posts 442. The frame member 440 is shown situated just below a wireform assembly 441 in FIG. 15A. As seen in FIGS. 15C-15D, the annulus band region 444 and the in-flow strut region 446 are exactly same as that of the frame member 402. The only difference is separate commissure posts 442 preferably made of plastic material that will be sewn together with the frame member 440 using sutures 448 before being covered with cloth. A pair of attachment holes 450 is desirably formed in each of the commissure posts 442 for this purpose. As before, the crimpable and expandable frame member 440 without commissure posts is laser-cut and electropolished.

Figure 18:
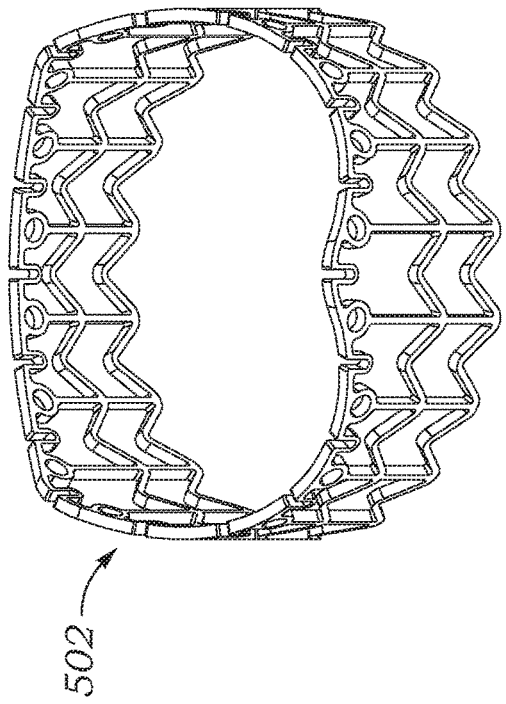
FIG. 18 is an elevational view of an integrated frame member similar to that shown in FIG. 16 with the polymer band overlapping an upper edge of the expandable frame.

FIG. 14A is a fully integrated frame member 402, with concerns over stiffened commissure posts. The frame member 442 shown in FIG. 15A alleviated that concern with three separate commissure posts 442, but those require sewing together with the expandable frame, which increases the time and steps when assembling the valve. In order to preserve the same load bearing characteristics of the existing commercial valve platforms, while still having a relative easy valve assembly procedure, the embodiments shown in FIGS. 16 and 18 are also contemplated.

Figure 17A:
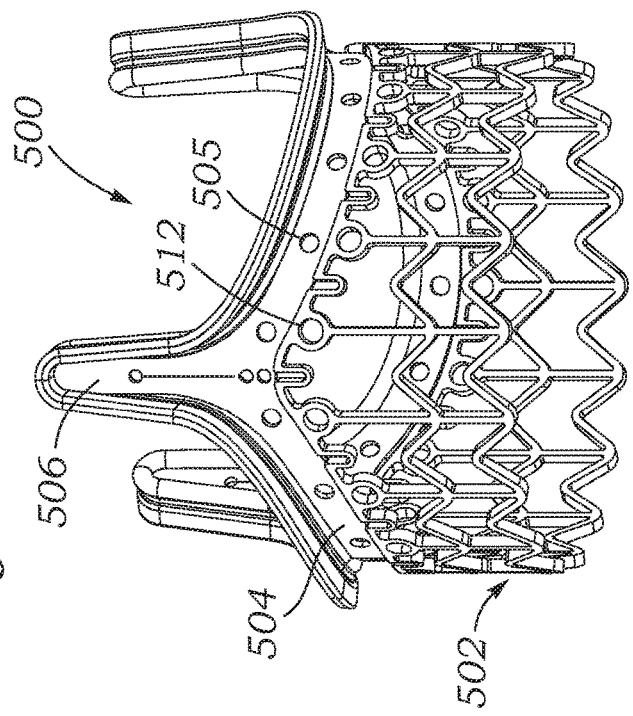
FIGS. 17A and 17B are elevational and perspective views of an exemplary expandable frame for use in the frame member of FIG. 16.
Figure 17B:
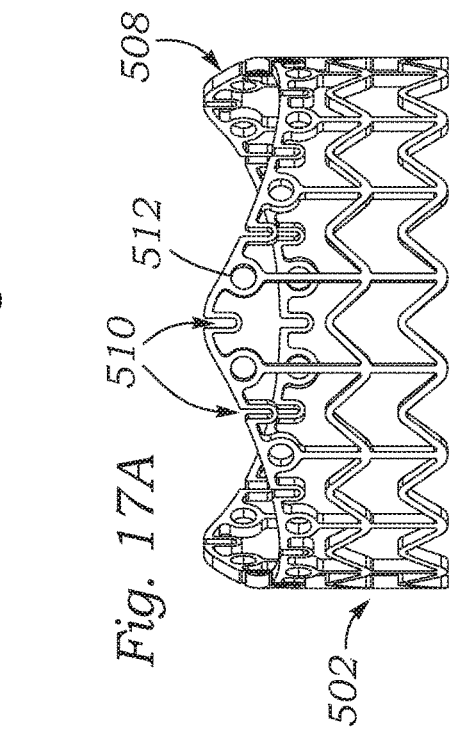

FIG. 16 shows an assembly 500, which includes an expandable frame 502 much like the frame 176 described above with respect to FIG. 9A, and seen in isolation in FIGS. 17A and 17B. The frame 502 is secured via sutures to a stent band 504 with upstanding commissures 506 to form an integrated frame member. This stent band 504 is essentially the inner band 95 from FIG. 4D, with suture holes 505 around its circumference to enable secure attachment to the top row of struts of the frame 502. An upper row of struts 508 includes regularly spaced compressible/expandable segments 510 to enable pre-implant compression, and post-implant expansion during a valve-in-valve procedure.

The assembly 500 is again crimpable and expandable. The stent band 504 is formed of a polymer (e.g., polyester) material that is breakable when an expansion force is applied within the valve. This makes the whole valve expandable for valve-in-valve applications. Because of the polymer commissures 506, the valve load carrying characteristics will be exactly the same as the existing commercial valve platform, thus hydrodynamic performance and durability of the valve shall be the same as the existing commercial valve as well. The relative position of the polyester band and the expandable frame can be assembled as illustrated in FIG. 16, with the stent band 504 positioned immediately above the frame member 502. Conversely, as seen in FIG. 18, the stent band 504 may be located partly radially within the frame 502, in an overlapping manner. This aligns the series of through holes 505 in the stent band 504 with eyeholes 512 provided in the frame 502 that greatly facilitates assembly, thus reducing time and expense.

While the disclosure references particular embodiments, it will understood that various changes and additional variations may be made and equivalents may be substituted for elements thereof without departing from the scope or the inventive concept thereof. In addition, many modifications may be made to adapt a particular situation or device to the teachings herein without departing from the essential scope thereof. Therefore, it is intended that the disclosure not be limited to the particular embodiments disclosed herein, but includes all embodiments falling within the scope of the appended claims.

What is claimed is:

1. A hybrid prosthetic heart valve adapted for post-implant expansion and having an inflow end and an outflow end, comprising:
    a valve member including an inner structural support stent having upstanding commissure posts extending in the outflow direction alternating with arcuate inflow cusps, and an inflow end undulating up and down corresponding to the commissure posts and cusps, the support stent having a continuous circumferential base defining an implant circumference that is non-compressible in normal physiological use and has a first diameter, and wherein the support stent permits expansion from the first diameter to a second diameter larger than the first diameter upon application of an outward dilatory force from within the support stent substantially larger than forces associated with normal physiological use, and a plurality of flexible leaflets having peripheral edges attached along the commissure posts and inflow cusps of the support stent and configured to ensure one-way blood flow through the valve member; and
    a plastically-expandable inflow stent frame secured to and projecting from an inflow end of the support stent and having a strength requiring a predetermined expansion force to convert to an expanded state, wherein the inflow stent frame comprises a plurality of expandable struts, and further wherein an upper edge extends continuously around a periphery of the inflow stent frame and defines an implant circumference with a nominal diameter that enables physiological functioning of the valve member when implanted, and wherein the upper edge is configured to expand only a limited amount from the nominal diameter to an enlarged diameter larger than the nominal diameter upon application of an outward dilatory force from within the outflow end substantially larger than forces associated with normal physiological use, and wherein the upper edge undulates with peaks and valleys to at least partially conform to the inflow end of the support stent.

2. The prosthetic heart valve of claim 1, wherein the support stent includes a radially outer band located concentrically around and attached to a radially inner band, the radially outer band having a single expandable segment formed by overlapping free ends and separated by a sliding insert, and further including a flexible sleeve surrounding the overlapping free ends of the outer band to maintain alignment of the free ends.

3. The prosthetic heart valve of claim 2, wherein the single expandable segment is located at one of the cusps of the support stent and the inner band is configured to expand below each of the commissure posts when the outer band expands.

4. The prosthetic heart valve of claim 1, further including a unique identifier on the support stent visible from outside the body after implant that identifies the support stent as being expandable.

5. The prosthetic heart valve of claim 1, wherein the upper edge has limited radially compressibility to enable compression of the inflow stent frame during delivery of the heart valve.

6. The prosthetic heart valve of claim 1, wherein the inflow stent frame is configured to expand below each of the support stent commissures upon application of the outward dilatory force.

7. The prosthetic heart valve of claim 6, wherein the inflow stent frame has a series of axial slits below each of the commissure posts that permit expansion of the outflow end upon application of the outward dilatory force.

8. The prosthetic heart valve of claim 6, wherein the inflow stent frame has a series of compression sections including spaces that enable a limited compression of the circumferential structure.

9. The prosthetic heart valve of claim 1, wherein the support stent includes a radially thin band that has a single expandable segment in the circumferential base.

10. The prosthetic heart valve of claim 1, wherein the support stent includes a radially thin band that has multiple expandable segments distributed around the circumferential base.

11. The prosthetic heart valve of claim 10, wherein the multiple expandable segments are aligned with each of the commissure posts.

12. A hybrid prosthetic heart valve adapted for post-implant expansion and having an inflow end and an outflow end, comprising:

a valve member including an inner structural support stent having upstanding commissure posts extending in the outflow direction alternating with arcuate inflow cusps, and an inflow end undulating up and down corresponding to the commissure posts and cusps, the support stent having a continuous circumferential base defining an implant circumference that is non-compressible in normal physiological use and has a first diameter, and wherein the support stent permits expansion from the first diameter to a second diameter larger than the first diameter upon application of an outward dilatory force from within the support stent substantially larger than forces associated with normal physiological use, and a plurality of flexible leaflets having peripheral edges attached along the commissure posts and inflow cusps of the support stent and configured to ensure one-way blood flow through the valve member; and a plastically-expandable inflow stent frame secured to and projecting from an inflow end of the support stent and having a strength requiring a predetermined expansion force to convert to an expanded state, and wherein an outflow end of the stent frame is formed by an outflow row strut that extends continuously around a periphery of the inflow stent frame and defines an implant circumference with a nominal diameter that enables physiological functioning of the valve member when implanted, and wherein the outflow row strut has a series of spaced V-shaped notches that permit limited expansion and contraction.

13. The prosthetic heart valve of claim 12, wherein the outflow row strut has limited radially compressibility of between about 7-20% of the nominal diameter to reduce the size of the outflow end during delivery of the heart valve.

14. The prosthetic heart valve of claim 12, wherein the support stent includes a radially outer band located concentrically around and attached to a radially inner band having a single expandable segment formed by overlapping free ends located at one of the cusps and separated by a sliding insert, and further including a flexible sleeve surrounding the overlapping free ends of the outer band to maintain alignment of the free ends.

15. The prosthetic heart valve of claim 14, wherein the single expandable segment is located at one of the cusps of the support stent and the inner band is configured to expand below each of the commissure posts when the outer band expands.

16. The prosthetic heart valve of claim 12, further including a unique identifier on the support stent visible from outside the body after implant that identifies the support stent as being expandable.

17. The prosthetic heart valve of claim 12, wherein the support stent includes a radially thin band that has a single expandable segment in the circumferential base.

18. The prosthetic heart valve of claim 12, wherein the support stent includes a radially thin band that has multiple expandable segments distributed around the circumferential base.

19. The prosthetic heart valve of claim 18, wherein the multiple expandable segments are aligned with each of the commissure posts.

* * * * *